(12) United States Patent
Shin

(10) Patent No.: US 12,086,987 B2
(45) Date of Patent: Sep. 10, 2024

(54) APPARATUS FOR PROVIDING EVALUATION OF BEDSORE STAGES AND TREATMENT RECOMMENDATIONS USING ARTIFICIAL INTELLIGENCE AND OPERATION METHOD THEREOF

(71) Applicant: FINEHEALTHCARE, Seoul (KR)

(72) Inventor: Hyun Kyung Shin, Seoul (KR)

(73) Assignee: FINEHEALTHCARE, Seoul (KR)

( * ) Notice: Subject to any disclaimer, the term of this patent is extended or adjusted under 35 U.S.C. 154(b) by 375 days.

(21) Appl. No.: 17/693,667

(22) Filed: Mar. 14, 2022

(65) Prior Publication Data

US 2022/0301171 A1    Sep. 22, 2022

(30) Foreign Application Priority Data

Mar. 16, 2021    (KR) .................. 10-2021-0033792

(51) Int. Cl.
*G06T 7/00*    (2017.01)
*A61B 5/00*    (2006.01)
(Continued)

(52) U.S. Cl.
CPC .......... *G06T 7/0016* (2013.01); *A61B 5/0077* (2013.01); *A61B 5/447* (2013.01);
(Continued)

(58) Field of Classification Search
CPC ............. G06T 7/0016; G06T 7/74; G06T 2207/20081; G06T 2207/20084; G06T 2207/30088; A61B 5/0077; A61B 5/447; A61B 5/4842; A61B 5/7267; A61B 5/445; A61B 5/4836; A61B 5/7264;
(Continued)

(56) References Cited

U.S. PATENT DOCUMENTS 11,568,976 B1 *  1/2023  Rockne ................. G16H 40/63
11,672,614 B1 *  6/2023  Roh ..................... A61B 5/4504
                                                              382/153
(Continued)

FOREIGN PATENT DOCUMENTS

KR    1020120072701 A    7/2012
KR    1020160092013 A    8/2016
(Continued)

*Primary Examiner* — Md K Talukder
(74) *Attorney, Agent, or Firm* — Dinsmore & Shohl LLP; Yongsok Choi, Esq.

(57) ABSTRACT

Provided are a device for managing bedsores and an operating method of the same. The operating method includes acquiring image data of a plurality of existing bedsores, acquiring existing bedsore-related information corresponding to the image data of the plurality of existing bedsores, training a convolutional neural network (CNN) with relationships between the image data of the plurality of existing bedsores and the existing bedsore-related information to acquire a machine learning model, acquiring bedsore image data of a current patient, applying the machine learning model to the bedsore image data of the current patient to determine information on a bedsore or bedsore treatment information of the current patient, and outputting the information on the bedsore or the bedsore treatment information of the current patient.

12 Claims, 12 Drawing Sheets

(51) Int. Cl.
*G06T 7/73* (2017.01)
*G06V 10/774* (2022.01)
*G06V 10/82* (2022.01)

(52) U.S. Cl.
CPC .......... *A61B 5/4842* (2013.01); *A61B 5/7267* (2013.01); *G06T 7/74* (2017.01); *G06V 10/7747* (2022.01); *G06V 10/82* (2022.01); *G06T 2207/20081* (2013.01); *G06T 2207/20084* (2013.01); *G06T 2207/30088* (2013.01)

(58) Field of Classification Search
CPC .. A61B 5/7465; G06V 10/7747; G06V 10/82; G06V 10/32; G06V 10/774; G06V 2201/03; A61F 13/00; A61F 2013/00404; G16H 30/40; G16H 50/20; G16H 70/20
See application file for complete search history.

(56) References Cited

U.S. PATENT DOCUMENTS

| | | | | |
|---|---|---|---|---|
| 2016/0022371 | A1* | 1/2016 | Sauer | G16H 30/40 600/407 |
| 2016/0364857 | A1* | 12/2016 | Reicher | G06V 10/764 |
| 2018/0144466 | A1* | 5/2018 | Hsieh | G06T 7/0012 |
| 2019/0150857 | A1* | 5/2019 | Nye | G16H 30/40 |
| 2019/0164285 | A1* | 5/2019 | Nye | G16H 10/60 |
| 2020/0193597 | A1 | 6/2020 | Fan et al. | |
| 2021/0290152 | A1* | 9/2021 | Vogel | G16H 40/67 |
| 2022/0313658 | A1* | 10/2022 | Mascharak | A61P 17/14 |

FOREIGN PATENT DOCUMENTS

| | | |
|---|---|---|
| KR | 1020200102961 A | 9/2020 |
| WO | 2015084462 A1 | 6/2015 |

* cited by examiner

APPARATUS FOR PROVIDING EVALUATION OF BEDSORE STAGES AND TREATMENT RECOMMENDATIONS USING ARTIFICIAL INTELLIGENCE AND OPERATION METHOD THEREOF

CROSS-REFERENCE TO RELATED APPLICATION

This application claims priority to and the benefit of Korean Patent Application No. 10-2021-0033792, filed on Mar. 16, 2021, the disclosure of which is incorporated herein by reference in its entirety.

BACKGROUND

1. Field of the Invention

The present disclosure relates to a device for managing bedsores and an operating method of the same.

2. Discussion of Related Art

A bedsore is a skin ulcer that is caused on a patient's back, waist, shoulders, elbows, or anus around the buttocks caused by contact with the lower surface because blood flow under the skin pressed by the weight of the patient is not smooth. In general, bedsores develop in patients who are hospitalized for a long time or patients who cannot freely change their position due to a cerebrospinal nerve disorder. Also, bedsores develop when the skin is compressed by a splint or cast. Bedsores are mainly caused when the skin is continuously pressed against a hard substance, moisture is present in a region where the skin is pressed and poorly ventilated, or the patient lacks proper nutrition or is in a poor hygiene or health state.

When a bedsore develops, blood flow at the pressed region deteriorates. Accordingly, the region first goes pale, the surroundings become red, and pressure pain develops. When the symptom worsens, a blister (a bulla) forms. When the bedsore further develops, the region becomes dark, and an ulcer forms in the area in which gangrene develops. Then, a foul-smelling discharge is produced, and the bedsore reaches a dangerous level.

A bedsore is a chronic disease and should be managed for a long period of time. Accordingly, in many cases, home care and outpatient treatment are combined rather than inpatient treatment, but there is a problem in that most target patients have difficulty moving to receive outpatient treatment due to characteristics of the illness.

For this reason, it is desperately necessary to develop a technology that relieves the inconvenience of a target patient suffering from bedsores and reduces economic and social costs by enabling the patient to manage and heal his or her bedsores without receiving outpatient treatment or inpatient treatment.

Meanwhile, in the field of medical image technology, the use of artificial intelligence (AI) technology is significantly increasing. In modern medical science, medical images are very essential tools for effective disease diagnosis and patient treatment. With the development of imaging technology, it has become possible to acquire more sophisticated medical image data, and the amount of data is gradually becoming vast. There is increasing demand for an AI technology for predicting a disease as well as treating a disease after the onset of the disease by systematically analyzing vastly collected medical data.

SUMMARY OF THE INVENTION

According to an aspect of the present disclosure, there is provided an operating method of a bedsore management device, the method including: acquiring image data of a plurality of existing bedsores; acquiring existing bedsore-related information corresponding to the image data of the plurality of existing bedsores; training a convolutional neural network (CNN) with relationships between the image data of the plurality of existing bedsores and the existing bedsore-related information to acquire a machine learning model; acquiring bedsore image data of a current patient; applying the machine learning model to the bedsore image data of the current patient to determine information on a bedsore or bedsore treatment information of the current patient; and outputting the information on the bedsore or the bedsore treatment information of the current patient. The existing bedsore-related information includes at least one of bedsore stage information and bedsore diagnosis information of the existing bedsores, the information on the bedsore of the current patient includes at least one of bedsore stage information and bedsore diagnosis information of the current patient, and the bedsore treatment information includes dressing information for treating a bedsore.

The training of the CNN with the relationships between the image data of the plurality of existing bedsores and the existing bedsore-related information to acquire the machine learning model may include: preprocessing the image data of the plurality of existing bedsores; extracting image feature data from the preprocessed image data; training a region-based convolutional neural network (R-CNN) with relationships between the image data of the plurality of existing bedsores and the bedsore stage information of the existing bedsores using the image feature data; and outputting information on relationships between the bedsore location information and the bedsore stage information of the plurality of existing bedsores.

The preprocessing of the image data of the plurality of existing bedsores may include performing annotation processing on the image data of the plurality of existing bedsores, and the training of the R-CNN with the relationships between the image data of the plurality of existing bedsores and the bedsore stage information of the existing bedsores may include using a region proposal network (RPN).

The applying of the machine learning model to the bedsore image data of the current patient to determine the information on the bedsore or the bedsore treatment information of the current patient may include determining dressing information required for treating the bedsore according to at least one of the bedsore stage information and the bedsore diagnosis information using a dressing recommendation algorithm.

The dressing recommendation algorithm may be determined using a deep decision tree boosting model.

According to another aspect of the present disclosure, there is provided a device for managing a bedsore, the device including a processor and a memory. On the basis of instructions stored in the memory, the processor performs: acquiring image data of a plurality of existing bedsores; acquiring existing bedsore-related information corresponding to the image data of the plurality of existing bedsores; training a CNN with relationships between the image data of the plurality of existing bedsores and the existing bedsore-related information to acquire a machine learning model; acquiring bedsore image data of a current patient; applying the machine learning model to the bedsore image data of the current patient to determine information on a bedsore and bedsore treatment information of the current patient; and outputting the information on the bedsore or the bedsore treatment information of the current patient. The existing bedsore-related information includes at least one of bedsore stage information, bedsore diagnosis information, and existing bedsore treatment information of the existing bedsores, the information on the bedsore of the current patient includes at least one of bedsore stage information and bedsore diagnosis information of the current patient, and the bedsore treatment information includes dressing information for treating the bedsore.

In order for the training of the CNN with the relationships between the image data of the plurality of existing bedsores and the existing bedsore-related information to acquire the machine learning model, on the basis of the instructions stored in the memory, the processor of the device may perform preprocessing the image data of the plurality of existing bedsores; extracting image feature data from the preprocessed image data; training an R-CNN with relationships between the image data of the plurality of existing bedsores and the bedsore stage information of the existing bedsores using the image feature data; and outputting information on relationships between bedsore location information and the bedsore stage information of the plurality of existing bedsores.

In order for the preprocessing of the image data of the plurality of existing bedsores, on the basis of the instructions stored in the memory, the processor may perform an annotation process on the image data of the plurality of existing bedsores, and in order for the training of the R-CNN with the relationships between the image data of the plurality of existing bedsores and the bedsore stage information of the existing bedsores, on the basis of the instructions stored in the memory, the processor may perform machine learning using an RPN.

In order for the applying of the machine learning model to the bedsore image data of the current patient and determine the information on the bedsore and the bedsore treatment information of the current patient, on the basis of the instructions stored in the memory, the processor may determine dressing information required for treating the bedsore according to at least one of the bedsore stage information and the bedsore diagnosis information using a dressing recommendation algorithm.

The dressing recommendation algorithm may be determined using a deep decision tree boosting model.

According to another aspect of the present disclosure, there is provided a program for implementing the operating method of a bedsore management device, the program being stored in a computer-readable recording medium.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION

Figure 1:
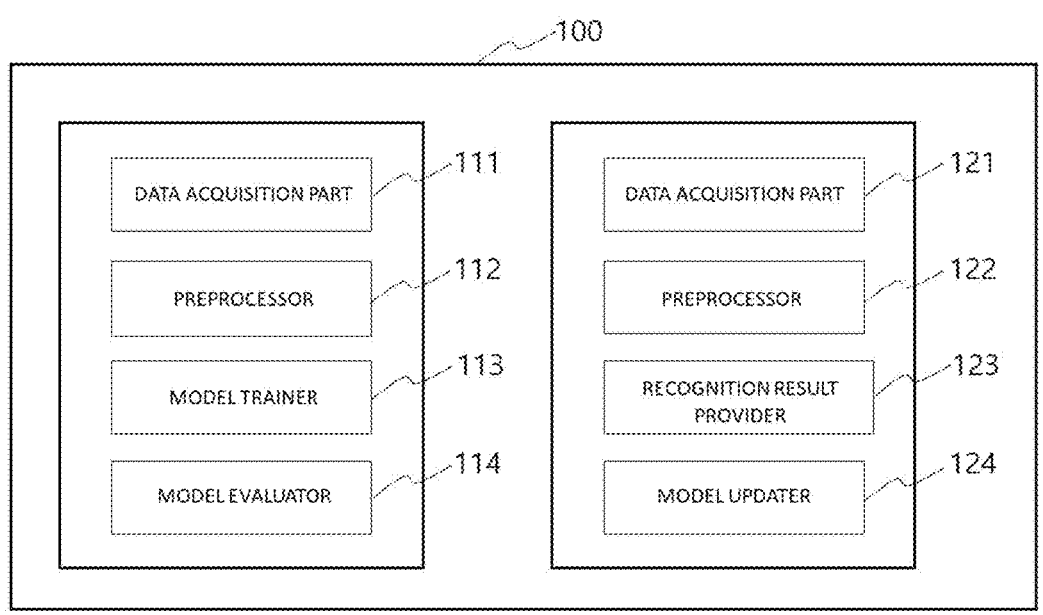
FIG. 1 is a block diagram of a bedsore management device (100) according to an exemplary embodiment of the present disclosure.

The advantages and features of the present disclosure and a method of achieving them will become apparent with reference to embodiments described in detail below with reference to the accompanying drawings. However, the present disclosure is not limited to the embodiments disclosed below and may be implemented in many different forms. The embodiments are only provided so that this disclosure will be thorough and complete and will fully convey the concept of the disclosure to those of ordinary skill in the art.

Terminology used herein will be described in brief, and then the disclosed embodiments will be described in detail.

Although terms used herein are selected from among general terms that are currently widely used in consideration of functionality in the present disclosure, these may be changed depending on intentions of those of ordinary skill in the art, precedents, the advent of a new technology, etc. Also, some terms are arbitrarily selected by the applicant for special cases, for which detailed meanings are explained in detail in the corresponding description of the disclosure. Therefore, terms used herein should be interpreted on the basis of their meanings and content of this overall disclosure rather than simply their names.

Unless clearly specified to be singular, singular expressions used herein include plurality. In addition, unless clearly specified to be plural, plural expressions include singularity.

Throughout the specification, when a part is said to "include" a component, this does not exclude other components and means that other components may also be included unless specifically described otherwise.

In addition, the term "unit" used herein refers to a software or hardware component. A "unit" plays a certain role. However, a "unit" is not limited to software or hardware. A "unit" may be configured to exist in an addressable storage medium or operate one or more processors. Accordingly, for example, "units" include components such as software components, object-oriented software components, class components, task components, processes, functions, attributes, procedures, subroutines, program code segments, drivers, firmware, microcode, circuitry, data, databases, data structures, tables, arrays, and variables. Functions provided within components and "units" may be combined into a smaller number of components and "units" or subdivided into additional components and "units."

According to an embodiment of the present disclosure, "units" may be implemented using a processor and a memory. The term "processor" is interpreted broadly to include a general-purpose processor, a central processing unit (CPU), a microprocessor, a digital signal processor (DSP), a controller, a microcontroller, a state machine, etc. In some environments, the term "processor" may refer to an application-specific integrated circuit (ASIC), a programmable logic device (PLD), a field programmable gate array (FPGA), etc. The term "processor" may, for example, also refer to a combination of a DSP and a microprocessor, a combination of multiple microprocessors, a combination of one or more microprocessors combined with a DSP core, or a combination of processing devices that is the same as other arbitrary combinations of such elements.

The term "memory" is interpreted broadly to include a random electronic component that may store electronic information. The term "memory" may also refer to various types of processor-readable media such as a random access memory (RAM), a read only memory (ROM), a non-volatile RAM (NVRAM), a programmable ROM (PROM), an erasable PROM (EPROM), an electrically erasable PROM (EEPROM), a flash memory, a magnetic or optical data storage device, a register, etc. When a processor may read information from a memory and/or record information on a memory, the memory is referred to as being in electronic communication with the processor. A memory integrated with a processor is in electronic communication with the processor.

Exemplary embodiments of the present disclosure will be described in detail below with reference to the accompanying drawings so that those of ordinary skill in the art may easily implement the embodiments. To clearly describe the present disclosure, parts irrelevant to the description are omitted in the drawings.

FIG. 1 is a block diagram of a bedsore management device 100 for according to an exemplary embodiment of the present disclosure.

Referring to FIG. 1, the bedsore management device 100 according to the exemplary embodiment may include a data learner 110 and a data recognizer 120. In addition, the bedsore management device 100 may include a processor and a memory.

The data learner 110 may receive first data and second data and acquire a machine learning model for the relationship between the first data and the second data. The machine learning model acquired by the data learner 110 may be a model for generating second data from first data. For example, the data learner 110 may learn the relationships between image data of a plurality of existing bedsores and existing bedsore-related information. When image data of a plurality of bedsores and information on the bedsores is given, the data learner 110 may generate a machine learning model for estimating bedsore treatment information. In the present disclosure, bedsore image data may be a two-dimensional (2D) image or a three-dimensional (3D) image.

The data recognizer 120 may apply image data of a bedsore of a current patient to the machine learning model and output bedsore-related information and/or bedsore treatment information. The machine learning model may include information on criteria for determining which treatment is recommended depending on a bedsore image. Also, the data recognizer 120 may use the bedsore image data and the result output by the machine learning model in updating the machine learning model.

At least one of the data learner 110 and the data recognizer 120 may be manufactured in the form of a hardware chip and mounted on an electronic device. For example, at least one of the data learner 110 and the data recognizer 120 may be manufactured in the form of a dedicated hardware chip for artificial intelligence (AI) or as a part of an existing general-purpose processor (e.g., a CPU or an application processor) or a graphics-only processor (e.g., a graphics processing unit (GPU)) and mounted on various electronic devices.

Also, the data learner 110 and the data recognizer 120 may be separately mounted on different electronic devices. For example, one of the data learner 110 and the data recognizer 120 may be included in an electronic device, and the other may be included in a server. In addition, the data learner 110 and the data recognizer 120 may be connected with or without wires to provide the machine learning model constructed by the data learner 110 to the data recognizer 120 or provide data input to the data recognizer 120 to the data learner 110 as additional training data.

Meanwhile, at least one of the data learner 110 and the data recognizer 120 may be implemented as a software module. When at least one of the data learner 110 and the data recognizer 120 is implemented as a software module (or a program module including instructions), the software module may be stored in the memory or a non-transitory computer-readable medium. In this case, the at least one software module may be provided by an operating system (OS) or a certain application. Alternatively, some of the at least one software module may be provided by an OS, and others may be provided by a certain application.

The data learner 110 according to an exemplary embodiment may include a data acquisition part 111, a preprocessor 112, a model trainer 113, and a model evaluator 114.

The data acquisition part 111 may acquire data required for machine learning. Since a large amount of data is required for machine learning, the data acquisition part 111 may receive the image data of the plurality of existing bedsores and the bedsore-related information corresponding to the image data of the plurality of existing bedsores.

According to an exemplary embodiment of the present disclosure, the bedsore-related information may include "bedsore stage information" which represents the development of a bedsore or the severity of a bedsore as a stage-specific value on the basis of a certain criterion of medical staff. Also, the bedsore-related information may additionally include "bedsore diagnosis information." For example, the bedsore diagnosis information may include at least one of whether the wound is serious, whether the edema is serious, the amount of necrotic tissue, the type of necrotic tissue, the degree of epithelialization, the amount of exudate, and information on a change in the skin around the wound, and may include score information obtained by scoring an evaluation thereof. According to an exemplary embodiment of the present disclosure, the bedsore diagnosis information may include score information about information used in a dressing recommendation algorithm of FIGS. 8 to 10 to be described below, for example, stage-specific questions of FIGS. 8 to 10.

The preprocessor 112 may preprocess image data of the acquired plurality of existing bedsores so that the received data may be used in machine learning. According to an exemplary embodiment of the present disclosure, the preprocessor 112 may annotate the bedsore image data with the bedsore-related information so that the model trainer 113 may use the bedsore image data, and may process the acquired image data in a preset format. For example, the preprocessor 112 may amplify and vectorize the bedsore image data by applying a filter to the data. Also, the preprocessor 112 may adjust at least one of the size, white balance, color, contrast, and saturation of the image data to clearly reveal features of the bedsores and may clearly reveal the outlines of the bedsores by applying a filter.

The image data preprocessed by the preprocessor 112 may be provided to the model trainer 113. According to an exemplary embodiment of the present disclosure, the model trainer 113 may learn relationships between the image data of the existing bedsores and the corresponding bedsore-related information. For example, the model trainer 113 may learn relationships between bedsore stage information and bedsore location information, for example, information about where the bedsores are located on patients' bodies, or coordinate information representing areas of the bedsores extracted from the image data of the bedsores. Also, the model trainer 113 may acquire a machine learning model that outputs bedsore-related information and/or bedsore treatment information according to image data of an existing bedsore. The model trainer 113 may train the machine learning model using the image data of the existing bedsores, the bedsore-related information, and bedsore treatment information as training data. The machine learning model may be a model built in advance. For example, the machine learning model may be a model that is built in advance by receiving default training data (e.g., bedsore image data, bedsore location information, bedsore stage information, bedsore diagnosis information, bedsore treatment information, etc.).

The machine learning model may be built in consideration of an application field of the machine learning model, a purpose of learning, computing performance of the device, etc. The machine learning model may be, for example, a model based on a neural network. As an example, models such as a deep neural network (DNN), a recurrent neural network (RNN), a long short-term memory model (LSTM), a bidirectional recurrent deep neural network (BRDNN), and a convolutional neural network (CNN) may be used as the machine learning model, but the machine learning model is not limited thereto.

According to various embodiments, when there are a plurality of machine learning models built in advance, the model trainer 113 may determine a machine learning model that is highly associated with input training data and the default training data as a machine learning model to be trained. In this case, the default training data may be already classified by data type. For example, default training data may be classified in advance by various criteria, such as a place where training data is generated, a time when training data is generated, a size of training data, a generator of training data, a type of object in training data, etc.

The model trainer 113 may train the machine learning model using a training algorithm and the like including, for example, error backpropagation or gradient descent.

The model trainer 113 may train the machine learning model through, for example, supervised learning in which training data is used as input values. Also, the model trainer 113 may train the machine learning model through unsupervised learning for finding criteria for situation judgment by self-learning the types of data required for situation judgment without any guidance. In addition, the model trainer 113 may learn the machine learning model through, for example, reinforcement learning using feedback on whether the result of situation judgment based on learning is correct.

When the machine learning model is trained, the model trainer 113 may store the trained machine learning model. In this case, the model trainer 113 may store the trained machine learning model in the memory of an electronic device including the data recognizer 120. Alternatively, the model trainer 113 may also store the trained machine learning model in the memory of a server connected to the electronic device through a wired or wireless network.

The memory in which the trained machine learning model is stored may also store commands or data related to at least one other component of the electronic device. Also, the memory may store software and/or programs. The programs may include, for example, a kernel, middleware, an application programming interface (API), an application program (or "application"), etc.

The model evaluator 114 may input evaluation data to the machine learning model and cause the model trainer 113 to repeat training when a result output from the evaluation data does not meet a certain criterion. In this case, the evaluation data may be preset data for evaluating the machine learning model.

For example, when the number or ratio of pieces of evaluation data with an inaccurate recognition result to results of the trained machine learning model for the evaluation data exceeds a preset threshold value, the model evaluator 114 may evaluate that the certain criterion is not met. As an example, when the certain criterion is defined as a ratio of 2% and the trained machine learning model outputs incorrect recognition results for more than 20 pieces of evaluation data out of 1,000 pieces of evaluation data, the model evaluator 114 may evaluate that the trained machine learning model is inappropriate.

Meanwhile, when there are a plurality of trained machine learning models, the model evaluator 114 may evaluate whether each of the trained machine learning models meets the certain criterion and determine a model that meets the certain criterion as a final machine learning model. In this case, when a plurality of models meet the certain criterion, the model evaluator 144 may determine one model or a certain number of models preset in decreasing order of evaluation score as the final machine learning model. Details of the model evaluator 114 will be described below with reference to FIG. 12.

At least one of the data acquisition part 111, the preprocessor 112, the model trainer 113, and the model evaluator 114 in the data learner 110 may be manufactured in the form of at least one hardware chip and mounted on the electronic device. For example, at least one of the data acquisition part 111, the preprocessor 112, the model trainer 113, and the model evaluator 114 may be manufactured in the form of a dedicated hardware chip for AI or as a part of an existing general-purpose processor (e.g., a CPU or an application processor) or a graphics-only processor (e.g., a GPU) and mounted on various electronic devices.

Also, the data acquisition part 111, the preprocessor 112, the model trainer 113, and the model evaluator 114 may be mounted on one electronic device or separately mounted on different electronic devices. For example, some of the data acquisition part 111, the preprocessor 112, the model trainer 113, and the model evaluator 114 may be included in an electronic device, and others may be included in a server.

Also, at least one of the data acquisition part 111, the preprocessor 112, the model trainer 113, and the model evaluator 114 may be implemented as a software module. When at least one of the data acquisition part 111, the preprocessor 112, the model trainer 113, and the model evaluator 114 is implemented as a software module (or a program module including instructions), the software module may be stored on a non-transitory computer-readable medium. In this case, the at least one software module may be provided by an OS or a certain application. Alternatively, some of the at least one software module may be provided by an OS, and others may be provided by a certain application.

The data recognizer 120 according to an exemplary embodiment of the present disclosure may include a data acquisition part 121, a preprocessor 122, a recognition result provider 123, and a model updater 124.

The data acquisition part 121 may acquire the bedsore image data of the current patient and bedsore-related information of the current patient. The preprocessor 122 may preprocess the acquired bedsore image data of the current patient and the acquired bedsore-related information of the current patient so that the received data may be used in machine learning. For example, the preprocessor 122 may amplify and vectorize the bedsore image data by processing the data through a filter. Also, the preprocessor 122 may clearly reveal the outline of a bedsore and adjust at least one of white balance, color, contrast, and saturation of the bedsore image data.

The recognition result provider 123 may acquire result data by applying the data preprocessed by the preprocessor 122 as described above to the machine learning model. The recognition result provider 123 may output the result data as voice or text.

The model updater 124 may have the machine learning model updated on the basis of an evaluation on the recognition result provided by the recognition result provider 123. For example, the model updater 124 may cause the model trainer 113 to update the machine learning model by providing the recognition result provided by the recognition result provider 123 to the model trainer 113.

Meanwhile, at least one of the data acquisition part 121, the preprocessor 122, the recognition result provider 123, and the model updater 124 in the data recognizer 120 may be manufactured in the form of at least one hardware chip and mounted on the electronic device. For example, at least one of the data acquisition part 121, the preprocessor 122, the recognition result provider 123, and the model updater 124 may be manufactured in the form of a dedicated hardware chip for AI or as a part of an existing general-purpose processor (e.g., a CPU or an application processor) or a graphics-only processor (e.g., a GPU) and mounted on various electronic devices.

Also, the data acquisition part 121, the preprocessor 122, the recognition result provider 123, and the model updater 124 may be mounted on one electronic device or separately mounted on different electronic devices. For example, some of the data acquisition part 121, the preprocessor 122, the recognition result provider 123, and the model updater 124 may be included in an electronic device, and others may be included in a server.

Also, at least one of the data acquisition part 121, the preprocessor 122, the recognition result provider 123, and the model updater 124 may be implemented as a software module. When at least one of the data acquisition part 121, the preprocessor 122, the recognition result provider 123, and the model updater 124 is implemented as a software module (or a program module including instructions), the software module may be stored on a non-transitory computer-readable medium. In this case, the at least one software module may be provided by an OS or a certain application. Alternatively, some of the at least one software module may be provided by an OS, and others may be provided by a certain application.

Figure 2:
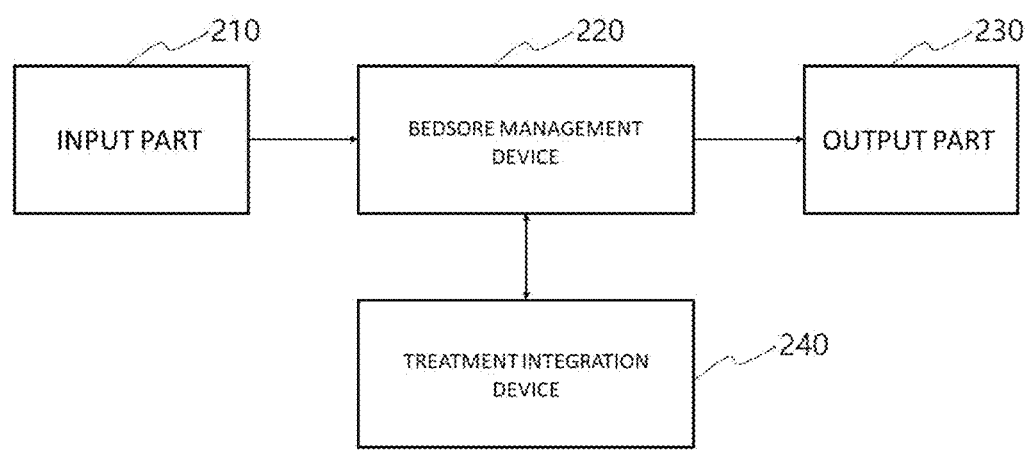
FIG. 2 is a diagram illustrating a bedsore management system according to an exemplary embodiment of the present disclosure.

FIG. 2 is a diagram illustrating a bedsore management system according to an exemplary embodiment of the present disclosure.

According to an exemplary embodiment of the present disclosure, a bedsore management system 200 may include an input part 210, a bedsore management device 220, and an output part 230. Also, the bedsore management system 200 may additionally include a treatment integration device 240.

The input part 210 may be included in a user terminal. The input part 210 may acquire image data of a bedsore. Also, the input part 210 may acquire bedsore-related information. The image data of the bedsore may be an image of the bedsore that is personally captured by the user through a camera. The image data of the bedsore may be obtained by photographing the bedsore but may also be image data of the bedsore included in image data obtained by photographing a special sheet on which the patient has lied, a dressing attached to the bedsore of the patient, or the patient's clothing. Unlike other wounds, the amount or color of exudate from the bedsore may have a strong correlation with the bedsore-related information. Accordingly, an image of exudate on the patient's clothes worn by the patient with the bedsore, an image of exudate on the dressing attached to the bedsore, or an image of exudate on a sheet on which the patient has lied may be used in predicting bedsore treatment information through a machine learning model. Also, the image of exudate on the patient's clothes and the image of exudate on the sheet on which the patient has lied may vary depending on a time for which the patient has lied there, and thus the input part 210 may additionally receive information related to a time for which the sheet, the dressing, or the patient's clothing has been used by the patient. The input part 210 may combine the time-related information with images. For example, the input part 210 may include the time-related information with metadata of the images. The time-related information may be used with the image data by the machine learning model.

The image data of the bedsore may be image data received by the user from another user terminal in a wired or wireless manner. The image data of the bedsore may be image data obtained by photographing the bedsore along with a cotton swab for showing the depth of the bedsore to measure the depth of the bedsore more precisely. The image data of the bedsore may be image data that has already been stored in the user terminal. As described above, the bedsore-related information input to the input part 210 may include bedsore stage information and/or bedsore diagnosis information.

The input part 210 may transmit the image data of the bedsore or the bedsore-related information to the bedsore management device 220 in a wired or wireless manner. The input part 210 may compress the image data of the bedsore or the bedsore-related information on the basis of a certain algorithm to reduce the volume of data.

The bedsore management device 220 may be included in the user terminal or a server. The bedsore management device 220 may perform machine learning on the basis of the data received from the input part 210 or output result data on the basis of the machine learning model that has already been trained. The bedsore management device 220 may output the machine learning model on the basis of the received image data of the bedsore or bedsore-related information. Also, the bedsore management device 220 may output the bedsore-related information and/or bedsore treatment information by applying the received image data of the bedsore to the machine learning model.

The bedsore management device 220 may transmit the generated machine learning model, the bedsore-related information, or the bedsore treatment information to the output part 230 in a wired or wireless manner. The bedsore management device 220 may compress the generated machine learning model, the bedsore-related information, or the bedsore treatment information using a certain algorithm to reduce the volume of data required for data transmission and increase a transmission rate.

The output part 230 may correspond to a user terminal. The output part 230 may be included in the same user terminal as the input part 210. The output part 230 may apply image data of a bedsore stored in the memory of the output part 230 to output bedsore-related information and/or bedsore treatment information. Also, the output part 230 may output the bedsore-related information and/or bedsore treatment information received from the bedsore management device 220. The output part 230 may output a result on a display or output a result as sound through a speaker. Operations of the bedsore management device 220 will be described below with reference to FIG. 3.

The treatment integration device 240 may receive bedsore-related information from the bedsore management device 220. For example, the treatment integration device 240 may receive at least one of the image data of the bedsore, bedsore location information, and the bedsore-related information from the bedsore management device 220. The treatment integration device 240 may display at least one of the image data of the bedsore, the bedsore location information, and the bedsore-related information so that medical staff may check the at least one of the image data of the bedsore, the bedsore location information, and the bedsore-related information. Also, the treatment integration device 240 may display a preset bedsore-related question to receive an answer to the bedsore-related question from the medical staff. The treatment integration device 240 may transmit received answer information to the bedsore management device 220. In addition to the answer information, the treatment integration device 240 may transmit bedsore-related information input by the medical staff to the bedsore management device 220. The treatment integration device 240 may be located in a medical institute, such as a hospital. In this case, the bedsore-related question may be received from an administrator who administers the bedsore management system 200 or the medical staff and set or may be set using a preset algorithm (e.g., a program and the like). Also, the bedsore-related question to which the medical staff will input an answer may include questions about bedsore diagnosis information, for example, whether the edema is serious, the amount of necrotic tissue, the amount of exudate, whether the patient has a high fever, whether the patient has been diagnosed with infection rather than fatigue or body aches, etc.

Figure 3:
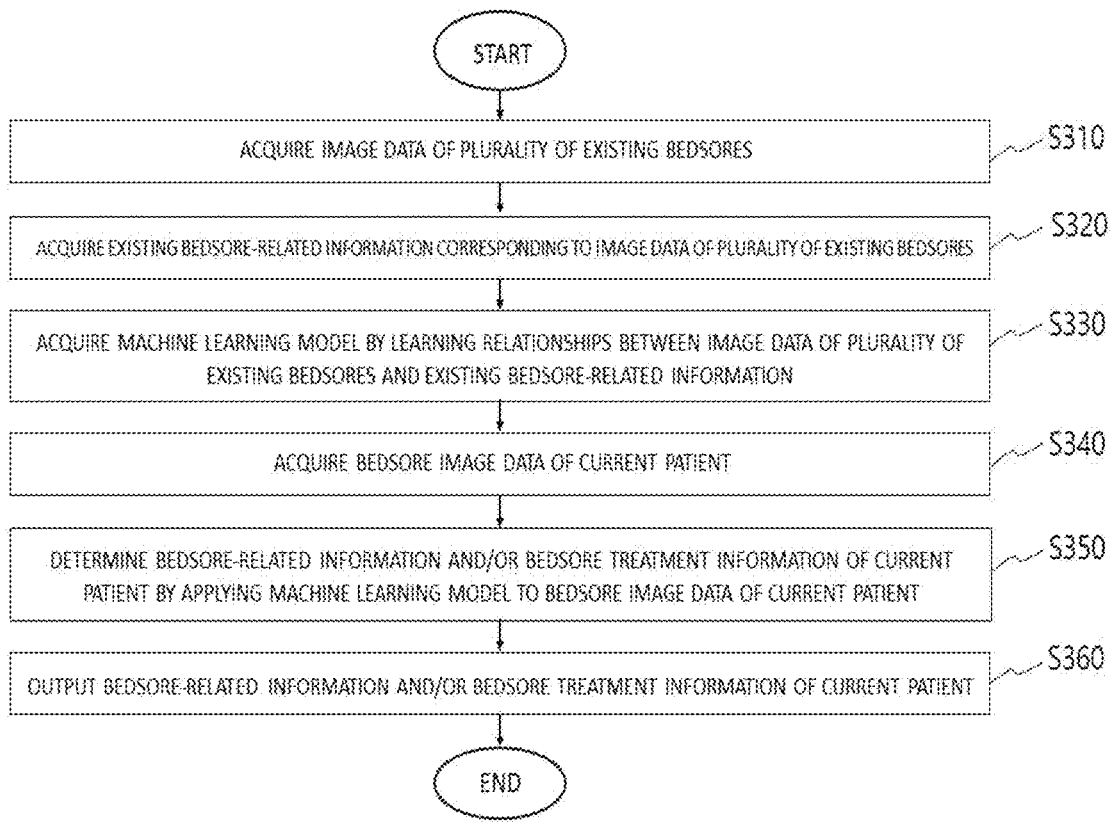
FIG. 3 is a flowchart illustrating operations of a bedsore management device according to an exemplary embodiment of the present disclosure.

FIG. 3 is a flowchart illustrating operations of a bedsore management device according to an exemplary embodiment of the present disclosure.

First, the bedsore management device 220 may acquire image data of a plurality of existing bedsores (S310). According to an exemplary embodiment of the present disclosure, the image data of the plurality of existing bedsores is image data acquired from bedsores of existing patients and may be input to the data acquisition part 111 shown in FIG. 1 and/or the input part 210 shown in FIG. 2. The image data of the plurality of existing bedsores may be images of the bedsores captured by medical staff while the medical staff treats the patient. The image data of the plurality of existing bedsores may be image data that clearly shows bedsore regions for use in machine learning. The image data of the plurality of existing bedsores may be image data obtained by photographing the bedsores but may also be images of exudate on patients' clothes, images of exudate on dressings attached to the bedsores, or images of exudate on sheets on which patients have lied. When the images of exudate on patients' clothes, the images of exudate on dressings attached to the bedsores, or the images of exudate on sheets on which patients have lied are received, the bedsore management device 220 may additionally receive information related to a time for which the sheets, the dressings, or the patient clothes have been used by the patients. The bedsore management device 220 may combine the time-related information with the image data. For example, the bedsore management device 220 may record the time-related information in metadata of the image data or convert a bit value of the time-related information into a bit value of at least one pixel and combine the time-related information with the images. When pixels included in an image have 16 bits, the bedsore management device 220 may represent the time-related information as 16×n bits, thereby converting the time-related information into pixel values. Here, n may be a natural number. The time-related information may be proportional to the pixel values. The time-related information and the image data may be used in generating a machine learning model. A user may select image data available for machine learning from among the image data of the plurality of existing bedsores.

According to an exemplary embodiment of the present disclosure, an annotation process may be performed on the image data of the plurality of existing bedsores. For example, the user may display bedsore regions as quadrangular boxes in the image data of the plurality of existing bedsores through a graphical user interface (GUI) of the input part 210 or the bedsore management device 220 and input bedsore stage information of the bedsores to the corresponding image data. When a quadrangular box is designated by an input of the user, the bedsore management device 220 may automatically designate coordinates of the quadrangular box. For example, the areas of the plurality of existing bedsores may be represented as coordinate information by showing positions of four vertices of the quadrangular boxes in x and y coordinates, and bedsore stage information previously input upon designation of the quadrangular boxes may correspond to the coordinate information. This will be described in further detail below with reference to FIG. 5.

Subsequently, the bedsore management device 220 may acquire existing bedsore-related information corresponding to the image data of the plurality of existing bedsores (S320).

According to an exemplary embodiment of the present disclosure, the user may input the bedsore-related information corresponding to the image data of the plurality of existing bedsores as well as the image data of the plurality of existing bedsores to the data acquisition part 111 shown in FIG. 1, or the input part 210 shown in FIG. 2. Alternatively, bedsore-related information input through the treatment integration device 240 shown in FIG. 2 may be transmitted to the bedsore management device 220. According to another exemplary embodiment of the present disclosure, the bedsore management device 220 may acquire bedsore-related information on the basis of the patients' medical records corresponding to the image data of existing bedsores or acquire bedsore-related information corresponding to the image data of the existing bedsores on the basis of results of existing diagnosis equipment, such as a laser Doppler. In this way, the bedsore management device 220 may acquire information from the treatment integration device 240. The bedsore-related information corresponding to the image data of the plurality of existing bedsores may include at least one of bedsore stage information, bedsore diagnosis information, location information of bedsores in the images, and bedsore treatment information. The bedsore-related information may include at least one of text and a number as an index. The bedsore-related information may be a ground truth value and label information. The bedsore-related information may be used for generating a machine learning model.

Subsequently, the bedsore management device 220 may learn relationships between the image data of the plurality of existing bedsores and the existing bedsore-related information, thereby acquiring a machine learning model (S330). This will be described in further detail below with reference to FIG. 4.

Subsequently, the bedsore management device 220 may acquire bedsore image data of a current patient (S340).

According to an exemplary embodiment of the present disclosure, the user may capture an image of a bedsore of the patient through a camera included in a user terminal and transmit the image to the bedsore management device 220. Alternatively, the user may transmit image data already stored in the memory to the bedsore management device 220. Otherwise, the user may transmit image data received from another terminal to the bedsore management device 220.

Subsequently, the bedsore management device 220 may determine information on the current patient's bedsores and/or bedsore treatment information by applying the machine learning model to the bedsore image data of the current patient (S350), and the determined information on the current patient's bedsores and/or the determined treatment information may be output to the output part 230 (S360).

According to an exemplary embodiment of the present disclosure, the bedsore management device 220 may determine information on the current patient's bedsores and/or bedsore treatment information by applying the machine learning model acquired in the above-described operation S330 to the bedsore image data of the current patient. This will be described in detail below with reference to FIG. 7.

Also, according to an exemplary embodiment of the present disclosure, the bedsore management device 220 may use a dressing recommendation algorithm in determining bedsore treatment information by applying the machine learning model to the bedsore image data of the current patient. This will be described in detail below with reference to FIGS. 8 to 11.

Figure 4:
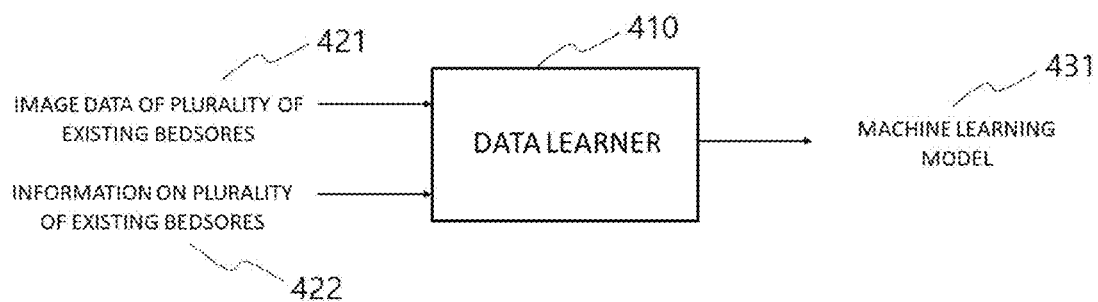
FIG. 4 is a block diagram illustrating a bedsore management device according to an exemplary embodiment of the present disclosure.

FIG. 4 is a block diagram illustrating a bedsore management device according to an exemplary embodiment of the present disclosure.

According to an exemplary embodiment of the present disclosure, the bedsore management device 220 may include a data learner 410. The data learner 410 of FIG. 4 may correspond to the data learner 110 of FIG. 1.

According to an exemplary embodiment of the present disclosure, the data learner 410 may acquire image data 421 of a plurality of existing bedsores. Also, the data learner 410 may acquire existing bedsore-related information 422 corresponding to each piece of the image data 421 of the plurality of existing bedsores. The existing bedsore-related information 422 may be label data. The existing bedsore-related information 422 may be determined by medical staff and input to the data learner 410. Alternatively, the existing bedsore-related information 422 may be stored in advance in the memory. The existing bedsore-related information 422 may be an index and include at least one of a number and text.

The data learner 410 may learn relationships between the image data 421 of the plurality of existing bedsores and the existing bedsore-related information 422 and output a machine learning model 431. As described above, the existing bedsore-related information 422 may include at least one of bedsore stage information, bedsore diagnosis information, location information of bedsores in the image data 421, and existing bedsore treatment information. The bedsore diagnosis information may include information used in the dressing recommendation algorithm of FIGS. 8 to 10 to be described below. For example, bedsore diagnosis information may include score information for stage-specific questions of the dressing recommendation algorithm of FIGS. 8 to 10 to be described below. The existing bedsore treatment information may be information on treatment corresponding to the image data 421 of the existing bedsores. The treatment may include information on dressing or information on medicine. According to an exemplary embodiment of the present disclosure, the bedsore management device 220 shown in FIG. 2 may store the machine learning model 431. Also, the bedsore management device 220 may transmit the machine learning model 431 to another bedsore management device. The bedsore management device 220 may acquire bedsore-related information and/or bedsore treatment information by applying image data of a new bedsore to the machine learning model 431.

Also, according to an exemplary embodiment of the present disclosure, the machine learning model 431 shown in FIG. 4 may perform both of machine learning for acquiring bedsore-related information and machine learning for acquiring bedsore treatment information. According to another exemplary embodiment of the present disclosure, the machine learning model 431 shown in FIG. 4 may include a machine learning model for acquiring bedsore-related information and a machine learning model for acquiring bedsore treatment information.

According to an exemplary embodiment of the present disclosure, the bedsore management device 220 may determine bedsore-related information or bedsore treatment information of a current patient by applying the machine learning model 431 to bedsore image data of the current patient. A process in which the bedsore management device 220 acquires bedsore-related information and/or bedsore treatment information using the machine learning model 431 will be described in detail below with reference to FIG. 7.

According to another exemplary embodiment of the present disclosure, the bedsore management device 220 may use sensor information as well as image data. For example, an olfactory sensor or a dust sensor may be attached near a patient. The bedsore management device 220 may periodically acquire sensor information from the olfactory sensor or the dust sensor. The sensor information may be displayed as a bit value. The bedsore management device 220 may combine the bit value of the sensor information with image data. For example, the bedsore management device 220 may convert the bit value of the sensor information into a bit value of at least one pixel and combine the converted bit value with an image. When pixels included in the image data have 16 bits, the sensor information may be represented as 16×n bits. Here, n may be a natural number. The bedsore management device 220 may perform machine learning on image data of existing bedsores including sensor information and existing bedsore-related information or bedsore treatment information. In this way, the bedsore management device 220 may acquire a machine learning model. The bedsore management device 220 may determine bedsore-related information or bedsore treatment information of a current patient by applying the machine learning model 431 to the bedsore image data of the current patient. In other words, the bedsore management device 220 may determine bedsore-related information or bedsore treatment information of the current patient by applying the machine learning model 431 to bedsore image data of the current patient. The bedsore image data of the current patient may be combined with sensor information using the above-described method.

A machine learning network for the data learner 410 shown in FIG. 4 to acquire the machine learning model 431 will be described below.

The data learner 410 shown in FIG. 4 may learn relationships between the image data of the plurality of existing bedsores and the existing bedsore-related information using a learning network employing a neural network to acquire the machine learning model 431.

According to an exemplary embodiment of the present disclosure, the network for the data learner 410 to learn the relationships between the image data of the plurality of existing bedsores and the existing bedsore-related information may be a CNN but is not limited thereto.

According to another exemplary embodiment of the present disclosure, the data learner 410 may learn the relationships between the image data of the plurality of existing bedsores and the existing bedsore-related information using a region-based CNN (R-CNN) to acquire the machine learning model 431.

According to another exemplary embodiment of the present disclosure, the data learner 410 may learn the relationships between the image data of the plurality of existing bedsores and the existing bedsore-related information using a faster R-CNN to acquire the machine learning model 431.

As a neural network which is a base of a machine learning model, there are various models, as is widely known. For example, representative neural networks include a CNN, a model improved from a CNN, etc. Among the various models, an R-CNN is a technology for classifying an object included in image data using a DNN.

Basically, a CNN is a network including several convolution layers and pooling layers. The CNN performs filtering on an input image through the convolution layers and extracts a feature map as a result. The feature map is used as an input to the next layer and thus is continuously processed by stages. The CNN outputs a classification or analysis result for the input image on the basis of the feature map of the input image.

The R-CNN is a model obtained by connecting a CNN which performs object analysis and a region proposal algorithm that proposes a region in which an object will be present in an image. The R-CNN determines a quadrangular candidate region using an algorithm, such as a selective search algorithm and the like, in an input image. The R-CNN cuts off candidate regions in the same size, extracts a feature from each region, and classifies an object.

Meanwhile, the faster R-CNN crops a feature map rather than an image itself and thus is fast. The faster R-CNN uses a region proposal network (RPN) which determines a candidate region. Specifically, the RPN is used for designating an object region in image data. In this way, regions other than an object to be recognized may be removed to recognize the object included in the image data.

According to an exemplary embodiment of the present disclosure, the data learner 410 may perform preprocessing including annotation on the acquired image data 421 of the plurality of existing bedsores and extract location information of bedsore regions through an image feature extraction operation, an RPN operation, and a detector operation for the image data vectorized through the preprocessing. Through this process, the data learner 410 may learn the relationships between bedsore location information and bedsore stage information. This will be described in detail below with reference to FIGS. 5 and 6.

Figure 5:
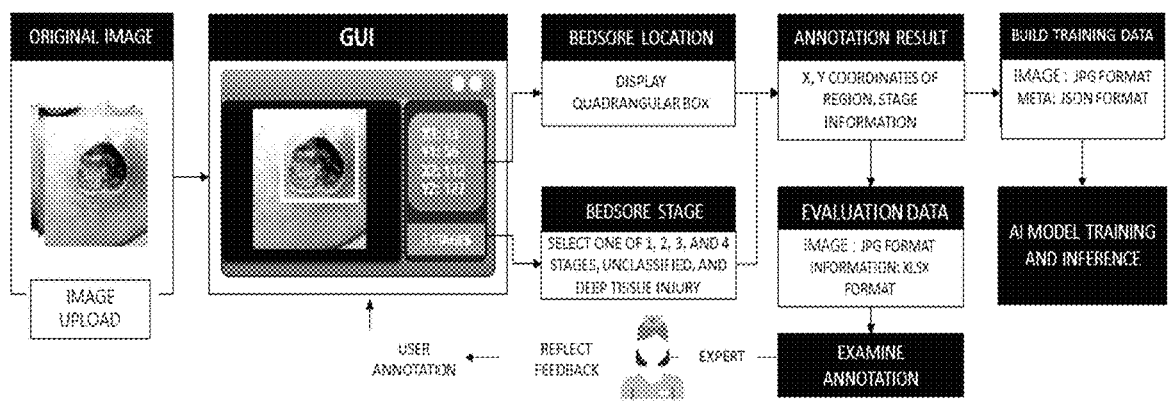
FIG. 5 is a diagram illustrating an example of an interface and a process for annotation processing on image data of an existing bedsore according to an exemplary embodiment of the present disclosure.

FIG. 5 is a diagram illustrating an example of an interface and a process for annotation processing on image data of an existing bedsore according to an exemplary embodiment of the present disclosure.

According to an exemplary embodiment of the present disclosure, the bedsore management device 220 may perform an annotation process of displaying bedsore location information and bedsore stage information regarding image data of a plurality of existing bedsores. Subsequently, the bedsore management device 220 may learn the annotated data and infer bedsore location information and bedsore stage information from image data of a bedsore. An exemplary embodiment of a process in which the bedsore management device 220 performs annotation processing on image data of a plurality of existing bedsores will be described below.

As shown in FIG. 5, image data of a plurality of existing bedsores and a GUI may be displayed through a user terminal. When a user designates bedsore regions in the image data of the existing bedsores through the GUI, coordinate information of bedsore locations may be input to the input part 210. Also, the user may input existing bedsore-related information through the GUI. For example, as shown in FIG. 5, the user may input bedsore stage information of the existing bedsores as existing bedsore-related information through the GUI. The input information may be acquired by the data acquisition part 111 shown in FIG. 1. Although not shown in FIG. 5, the user may additionally input diagnosis information of the existing bedsores.

As shown in FIG. 5, the user may display the bedsore regions as quadrangular boxes in the image data of the plurality of existing bedsores through the GUI. When a quadrangular box is input through the GUI, coordinates of X1, Y1, X2, and Y2 corresponding to four vertices of the quadrangular box may be automatically designated as shown in FIG. 5. This may be performed by the data acquisition part 111 or the preprocessor 112 shown in FIG. 1.

According to an exemplary embodiment of the present disclosure, the preprocessor 112 shown in FIG. 1 may convert a file format of the image data of the existing bedsores acquired from the data acquisition part 111. For example, as shown in FIG. 5, when the image data acquired by the data acquisition part 111 is in JPG or PNG format, the preprocessor 112 may convert the data into XLSX format or JSON format. The data converted into XLSX format may be used as data to be examined, and the data converted into JSON format may be used as training data in machine learning.

According to an exemplary embodiment of the present disclosure, at least one expert healthcare worker provides feedback on the data to be examined, thereby increasing accuracy in annotation processing. Specifically, at least one expert healthcare worker determines whether the image data of the existing bedsores and corresponding bedsore-related information appropriately match and provides feedback, and the user may input information updated with the feedback through the GUI.

Referring back to FIG. 4 described above, the image data 421 of the plurality of existing bedsores and the existing bedsore-related information 422 may be built as training data through the annotation processing as described above, input to the data learner 410, subjected to certain data preprocessing, and then used in machine learning. This will be described in detail below with reference to FIG. 6.

Although not shown in FIG. 4, the preprocessor 112 may annotate at least one of bedsore diagnosis information, bedsore assessment scores (Braden scale) and albumin levels, the conditions of wound bases and the amounts of exudate, the characteristics of each dressing material, and whether wounds are healed and the characteristics of the types of healing such that machine learning may be performed with various bedsore-related characteristics.

Figure 6:
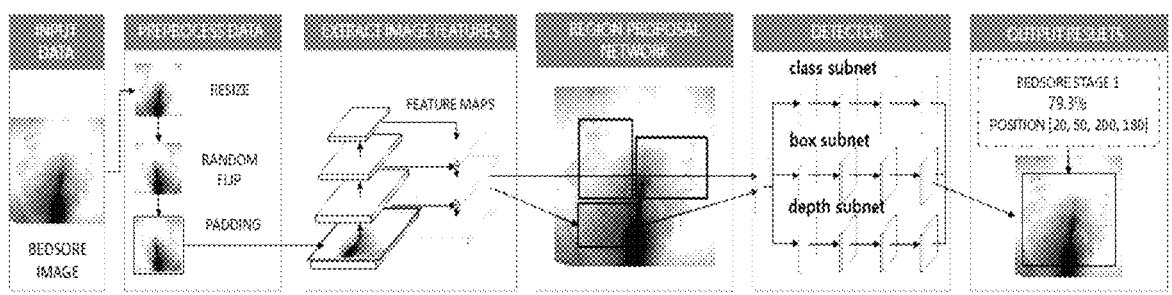
FIG. 6 is a diagram illustrating an example of an interface and a process for machine learning with image data of a plurality of existing bedsores according to an exemplary embodiment of the present disclosure.

FIG. 6 is a diagram illustrating an example of an interface and a process for machine learning with image data of a plurality of existing bedsores according to an exemplary embodiment of the present disclosure.

According to an exemplary embodiment of the present disclosure, image data of a plurality of existing bedsores, which has been converted into training data through annotation processing as described above with reference to FIG. 5, may undergo a process for machine learning in the data learner 410. For example, as shown in FIG. 6, the preprocessor 112 of the data learner 410 may first perform a preprocessing operation, an image feature extraction operation, an RPN operation, and a detector operation on input image data of a plurality of existing bedsores and output location information of the plurality of existing bedsores in the image data and stage information of the plurality of existing bedsores.

According to an exemplary embodiment of the present disclosure, first, the preprocessor 112 may amplify and process the image data of the plurality of existing bedsores in a vector form by applying an image filter to the image data so that the image data may be used in machine learning. For example, the preprocessor 112 may amplify the image data of the plurality of existing bedsores by applying at least one of bilateral, Gaussian, and histogram equalization filters to the image data of the existing bedsores.

Subsequently, as shown in FIG. 6, the preprocessor 112 may perform one or more processes among normalization, resizing, flipping, padding, scaling, translocation, rotation, perspective transformation, noise adjustment, lighting condition changing, and background and style changing on the amplified image data to vectorize the bedsore image data.

Here, normalization of the image data involves limiting the range of data to a range desired by a user to reduce scale difference which is a data characteristic. Resizing generates a changed appearance image through an object ratio adjustment in an object image and is used for generating an object image that has a similar appearance but looks different depending on the angle of view. Flipping generates an image by turning an object vertically or horizontally and is used for generating an object image in which an object shows the same appearance but looks different depending on the angle and direction of view. Scaling generates an object image in various sizes by changing an object image size and is used for generating an object image that shows the same appearance but looks different depending on the angle and distance of view. Translocation changes the background and location of an object image and is used for generating an object image in which an object shows a similar appearance but looks different depending on the location of view. Rotation generates images of various angles by rotating an image and is used for generating an object image in which an object shows a similar appearance but looks different depending on the angle of view. Perspective transformation generates an image by adjusting 3D angles (X axis, Y axis, and Z axis) at which an object is shown and is used for generating an object image that shows a similar appearance but looks different depending on the angle of view. Noise adjustment is used for generating image data that shows the same appearance but shows the external texture of an object at several levels. Light and condition changing generates an image by changing the brightness of an object image and is used for generating image data including several colors and shades depending on the brightness of light.

Subsequently, as shown in FIG. 6, the model trainer 113 may use a neural network on the image data vectorized by the preprocessor 112 and acquire a feature map of the bedsore image data through several scaling operations. Subsequently, the model trainer 113 may extract information on a region to be recognized, for example, a bedsore region, from the image data of existing bedsores by applying an RPN to the acquired feature map. In the operation of applying the RPN, binary classification may be performed on an anchor box having a certain aspect ratio on the basis of a specific position in the image using the acquired feature map of the image data.

Subsequently, as shown in FIG. 6, the model trainer 113 may apply the RPN and then apply a detector. In the operation of applying the detector, an RPN result and the feature map of the image data may be used for learning location-related information of the plurality of existing bedsores, for example, location coordinate information of bedsore regions, or depth information of the bedsores and bedsore-related information of the existing bedsores corresponding thereto, for example, bedsore stage information.

According to an exemplary embodiment of the present disclosure, the model trainer 113 may calculate a final loss value by adding an RPN loss value and a detector loss value, and parameters of the machine learning model may be updated to reduce the final loss value.

According to an exemplary embodiment of the present disclosure, to extract image features from the image data, the model trainer 113 may use a technology fused with a state of the art (SOTA) object recognition technology or use a common object in context (COCO) dataset.

Figure 7:
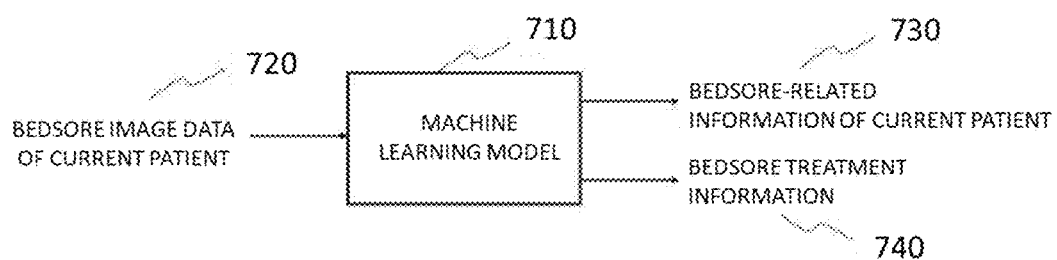
FIG. 7 is a block diagram illustrating a bedsore management device according to an exemplary embodiment of the present disclosure.

FIG. 7 is a block diagram illustrating a bedsore management device according to an exemplary embodiment of the present disclosure.

According to an exemplary embodiment of the present disclosure, the bedsore management device 220 shown in FIG. 2 may include the data recognizer 120 of FIG. 1. The data recognizer 120 shown in FIG. 1 may apply input data to a machine learning model 710 acquired in advance and acquire result data. Specifically, the bedsore management device 220 may apply bedsore image data 720 of a current patient to the machine learning model 710 and acquire bedsore-related information 730 of the current patient.

The bedsore image data of the current patient acquired by the bedsore management device 220 may be obtained by capturing a bedsore but may also be an image of exudate on the patient's clothes, an image of exudate on a dressing attached to the bedsore, or an image of exudate on a sheet on which the patient has lied. When the image of exudate on the patient's clothes, the image of exudate on the dressing attached to the bedsore, or the image of exudate on the sheet on which the patient has lied is received, the bedsore management device 220 may combine time-related information with the image data. For example, the bedsore management device 220 may record the time-related information in metadata of the image data or convert a bit value of the time-related information into a bit value of at least one pixel and combine the time-related information with the image. The process of combining the image data and the time-related information has been described above and thus will not be reiterated.

Also, the bedsore management device 220 may apply the bedsore image data 720 of the current patient to the machine learning model 710 and additionally acquire bedsore treatment information 740. The machine learning model 710 of FIG. 7 may correspond to the machine learning model 431 of FIG. 4.

When the machine learning model 431 of FIG. 4 performs machine learning on relationships between image data of existing bedsores and existing bedsore-related information, the machine learning model 431 may output bedsore-related information or bedsore treatment information of the current patient on the basis of the bedsore image data of the current patient in FIG. 7. This is because the existing bedsore-related information includes at least one of bedsore stage information of the existing bedsores, bedsore diagnosis information of the existing bedsores, bedsore location information of the existing bedsores in the image data 421, and existing bedsore treatment information.

The bedsore-related information 730 of the current patient that is acquired by the machine learning model 710 learning the bedsore image data 720 of the current patient may include bedsore stage information and/or diagnosis information. The bedsore diagnosis information of the current patient may include information used in the dressing recommendation algorithm of FIGS. 8 to 10 to be described below. For example, the bedsore diagnosis information of the current patient may include score information for stage-specific questions of the dressing recommendation algorithm of FIGS. 8 to 10 to be described below.

According to an exemplary embodiment of the present disclosure, the bedsore management device 220 may apply the bedsore image data 720 of the current patient to the machine learning model 710 and acquire various bedsore-related information. For example, the bedsore management device 220 may apply the bedsore image data 720 of the current patient to the machine learning model 710 and acquire bedsore location information and bedsore stage information. Also, the bedsore management device 220 may apply the bedsore image data 720 of the current patient to the machine learning model 710 and acquire diagnosis information about the current bedsore used in the dressing recommendation algorithm to be described with reference to FIGS. 8 to 10.

Further, the bedsore management device 220 may apply the acquired bedsore-related information 730 to the dressing recommendation algorithm to be described with reference to FIGS. 8 to 10 and acquire the bedsore treatment information 740.

However, a method for the bedsore management device 220 to acquire bedsore treatment information is not limited thereto, and the bedsore management device 220 may apply the bedsore image data of the current patient to the machine learning model 710 and generate bedsore treatment information.

In addition, diagnosis information to be input by a user or a healthcare worker, for example, whether the current patient has a high fever and whether the current patient has been diagnosed with infection rather than fatigue or body aches, may be input to the bedsore management device 220, and the input additional information may be used in determining the bedsore treatment information 740.

The bedsore management device 220 may apply the bedsore image data of the current patient including sensor information of the current patient to a machine learning model and acquire bedsore-related information or bedsore treatment information of the current patient. As described above, the sensor information may be information acquired from an olfactory sensor or a dust sensor. The sensor information may be combined with the bedsore image data of the current patient. A process of combining the sensor information with the bedsore image data has already been described above and thus will not be reiterated.

According to an exemplary embodiment of the present disclosure, the bedsore treatment information 740 may include dressing information required for bedsore treatment. A dressing for bedsore treatment may be determined by the dressing recommendation algorithm. The dressing recommendation algorithm will be described in detail below with reference to FIGS. 8 to 10.

The dressing recommendation algorithm of FIGS. 8 to 10 to be described below is an exemplary embodiment of the present disclosure and may be determined through machine learning. This will be described below with reference to FIG. 11.

Figure 8:
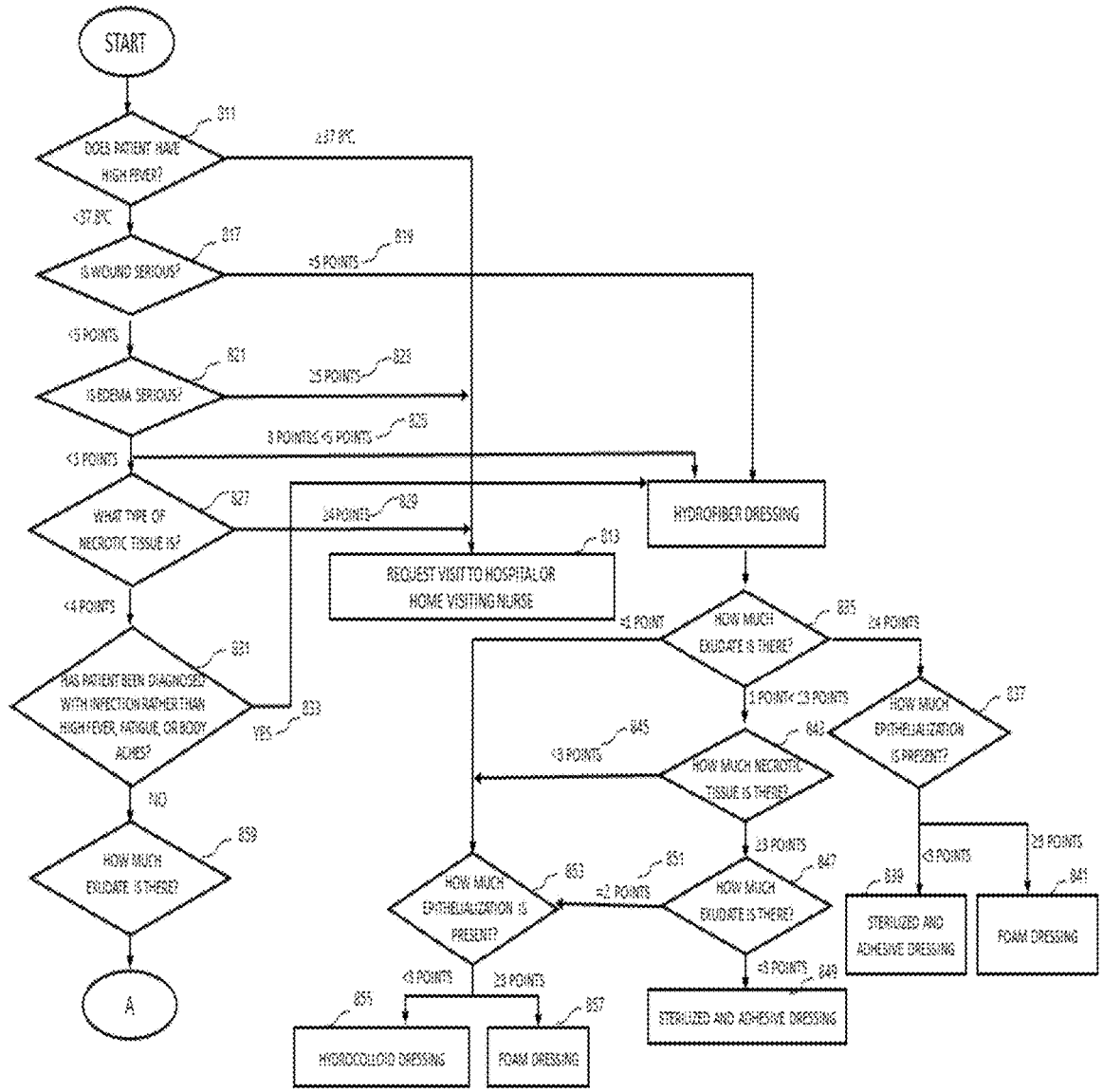
FIG. 8 is a flowchart illustrating a dressing recommendation algorithm according to an exemplary embodiment of the present disclosure.
Figure 9:
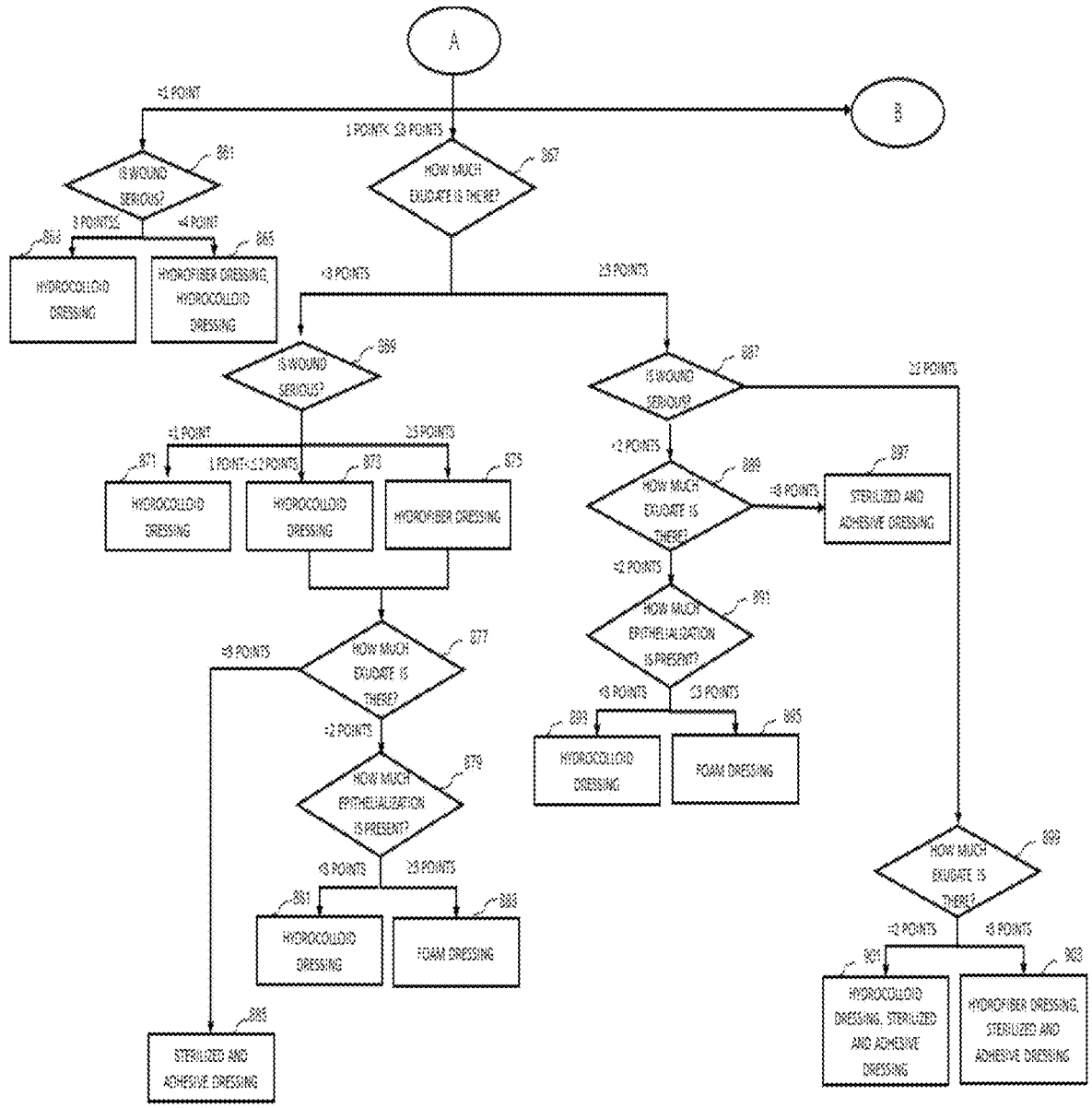
FIG. 9 is a flowchart illustrating a dressing recommendation algorithm according to an exemplary embodiment of the present disclosure.
Figure 10:
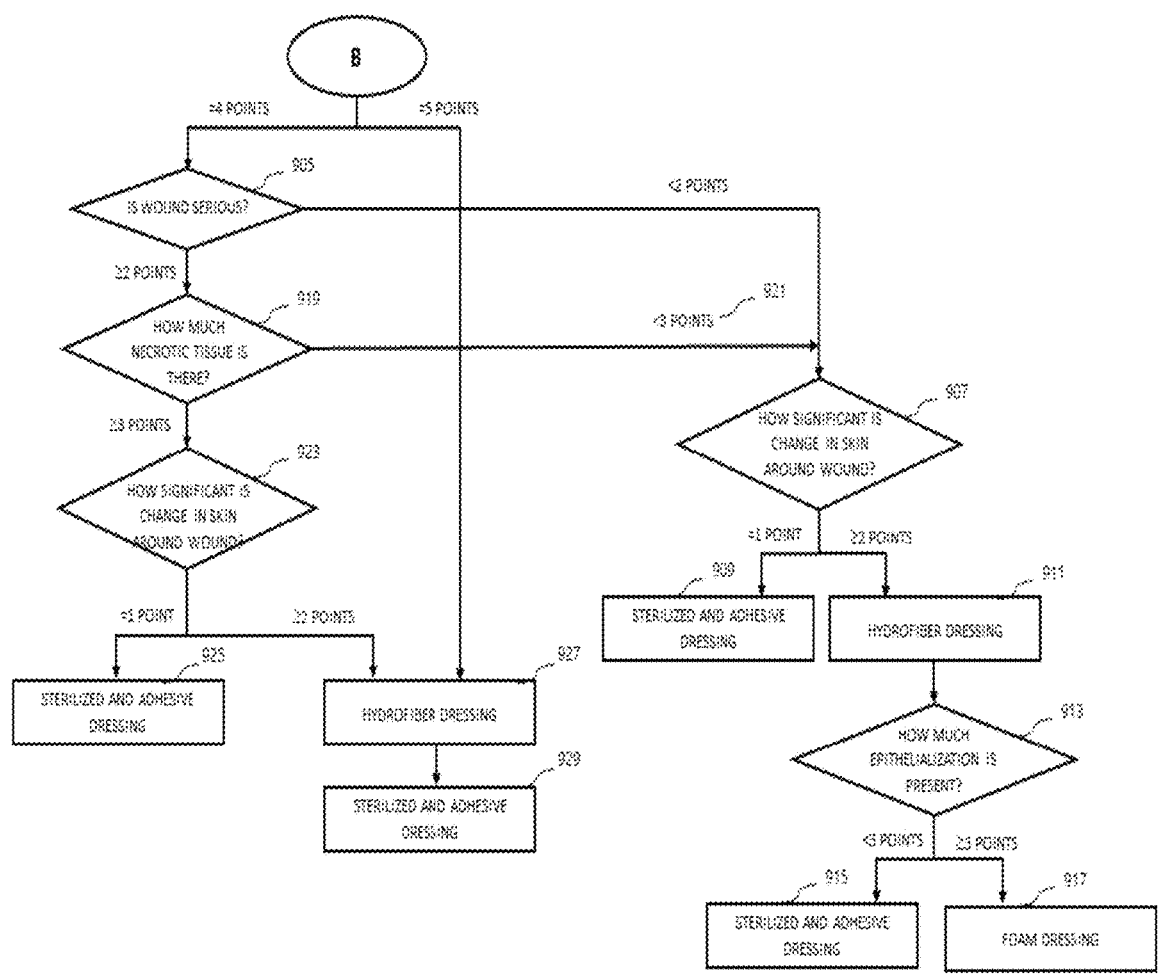
FIG. 10 is a flowchart illustrating a dressing recommendation algorithm according to an exemplary embodiment of the present disclosure.

FIGS. 8 to 10 are flowcharts illustrating a dressing recommendation algorithm according to an exemplary embodiment of the present disclosure.

Referring to FIGS. 8 to 10, the bedsore management device 220 determines whether a patient has a high fever using bedsore diagnosis information (811).

When the patient has a fever of 37.8° C. or higher, the bedsore management device 220 requests a visit to a hospital through a user terminal or requests a home visiting nurse through the treatment integration device 240 (813).

When the patient has a fever of less than 37.8° C., the bedsore management device 220 checks an answer acquired from the bedsore management device 220 and/or the treatment integration device 240 to the question of whether the wound is serious (817). The current bedsore diagnosis information may include the answer information to the question of whether the wound is serious. The bedsore management device 220 may acquire the answer information to the question of whether the wound is serious on the basis of the machine learning model 710. In other words, the bedsore management device 220 may apply the bedsore image data of the current patient to the machine learning model 710 and acquire the answer information to the question of whether the wound is serious.

When the answer to the question of whether the wound is serious is five points, the bedsore management device 220 sets medical dressing to hydrofiber dressing (819). A subsequent process will be described in an operation 835.

When the answer to the question of whether the wound is serious is less than five points, the bedsore management device 220 checks an answer acquired from the bedsore management device 220 and/or the treatment integration device 240 to the question of whether the edema is serious (821). The current bedsore diagnosis information may include the answer information to the question of whether the edema is serious. The bedsore management device 220 may acquire the answer information to the question of whether the edema is serious on the basis of the machine learning model 710. In other words, the bedsore management device 220 may apply the bedsore image data of the current patient to the machine learning model 710 and acquire the answer information to the question of whether the edema is serious.

When the answer to the question of whether the edema is serious is five points or more, the bedsore management device 220 requests a visit to a hospital through the user terminal or requests a home visiting nurse through the treatment integration device 240 (823).

When the answer to the question of whether the edema is serious is three points or more and less than five points, the bedsore management device 220 sets medical dressing to hydrofiber dressing (825). A subsequent process will be described in the operation 835.

When the answer to the question of whether the wound is serious is less than three points, the bedsore management device 220 checks an answer acquired from the bedsore management device 220 and/or the treatment integration device 240 to a question on the amount of necrotic tissue (827). The current bedsore diagnosis information may include the answer information to the question on the amount of necrotic tissue. The bedsore management device 220 may acquire the answer information to the question on the amount of necrotic tissue on the basis of the machine learning model 710. In other words, the bedsore management device 220 may apply the bedsore image data of the current patient to the machine learning model 710 and acquire the answer information to the question on the amount of necrotic tissue.

When the answer to the question on the amount of necrotic tissue is four points or more, the bedsore management device 220 requests a visit to a hospital through the user terminal or requests a home visiting nurse through the treatment integration device 240 (829).

When the answer to the question on the amount of necrotic tissue is less than four points, the bedsore management device 220 determines whether the patient has been diagnosed with infection rather than high fever, fatigue, and body aches using the bedsore diagnosis information (831).

When the patient has been diagnosed with infection rather than high fever, fatigue, and body aches, the bedsore management device 220 sets medical dressing to hydrofiber dressing (833)

The bedsore management device 220 checks an answer acquired from the bedsore management device 220 and/or the treatment integration device 240 to a question on the amount of exudate (835). The current bedsore diagnosis information may include the answer information to the question on the amount of exudate. The bedsore management device 220 may acquire the answer information to the question on the amount of exudate on the basis of the machine learning model 710. In other words, the bedsore management device 220 may apply the bedsore image data of the current patient to the machine learning model 710 and acquire the answer information to the question on the amount of exudate.

When the answer to the question on the amount of exudate is four points or more, the bedsore management device 220 checks an answer acquired from the bedsore management device 220 and/or the treatment integration device 240 to the question of how much epithelialization is present (837). The current bedsore diagnosis information may include the answer information to the question of how much epithelialization is present. The bedsore management device 220 may acquire the answer information to the question of how much epithelialization is present on the basis of the machine learning model 710. In other words, the bedsore management device 220 may apply the bedsore image data of the current patient to the machine learning model 710 and acquire the answer information to the question of how much epithelialization is present.

When the answer to the question of how much epithelialization is present is less than three points, the bedsore management device 220 sets medical dressing to sterilized and adhesive dressing (839).

When the answer to the question of how much epithelialization is present is three points or more, the bedsore management device 220 sets medical dressing to foam dressing (841).

When the answer to the question of how much epithelialization is present exceeds one point and is less than or equal to three points, the bedsore management device 220 checks an answer included in read result data to the question on the amount of necrotic tissue (843).

When the answer to the question on the amount of necrotic tissue is less than three points, the bedsore management device 220 checks an answer acquired from the bedsore management device 220 and/or the treatment integration device 240 to the question of how much epithelialization is present (845).

A subsequent process will be described in the operation 853.

When the answer to the question on the amount of necrotic tissue is three points or more, the bedsore management device 220 checks an answer acquired from the bedsore management device 220 and/or the treatment integration device 240 to the question on the amount of exudate (847).

When the answer to the question on the amount of exudate is three points, the bedsore management device 220 sets medical dressing to sterilized and adhesive dressing (849).

When the answer to the question on the amount of exudate is two points, the bedsore management device 220 checks an answer acquired from the bedsore management device 220 and/or the treatment integration device 240 to the question of how much epithelialization is present (851). A subsequent process will be described in the operation 853.

The bedsore management device 220 checks the answer acquired from the bedsore management device 220 and/or the treatment integration device 240 to the question of how much epithelialization is present (853).

When the answer to the question of how much epithelialization is present is less than three points, the bedsore management device 220 sets medical dressing to sterilized and adhesive dressing (855).

When the answer to the question of how much epithelialization is present is three points or more, the bedsore management device 220 sets medical dressing to foam dressing (857).

When the patient has not been diagnosed with infection rather than high fever, fatigue, and body aches, the bedsore management device 220 checks an answer acquired from the bedsore management device 220 and/or the treatment integration device 240 to the question on the amount of exudate (859).

When the answer to the question on the amount of exudate is one point, the bedsore management device 220 checks an answer acquired from the bedsore management device 220 and/or the treatment integration device 240 to the question of how deep the wound is (861). The current bedsore diagnosis information may include the answer information to the question of how deep the wound is. The bedsore management device 220 may acquire the answer information to the question of how deep the wound is on the basis of the machine learning model 710. In other words, the bedsore management device 220 may apply the bedsore image data of the current patient to the machine learning model 710 and acquire the answer information to the question of how deep the wound is.

When the answer to the question of how deep the wound is three points or less, the bedsore management device 220 sets medical dressing to hydrocolloid dressing (863).

When the answer to the question of how deep the wound is four points, the bedsore management device 220 sets medical dressing to hydrofiber dressing and hydrocolloid dressing (865).

When the answer to the question on the amount of exudate exceeds one point and is less than or equal to three points, the bedsore management device 220 checks an answer acquired from the bedsore management device 220 and/or the treatment integration device 240 to the question on the amount of necrotic tissue (867).

When the answer to the question on the amount of necrotic tissue is less than three points, the bedsore management device 220 checks an answer acquired from the bedsore management device 220 and/or the treatment integration device 240 to the question of how deep the wound is (869).

When the answer to the question of how deep the wound is one point, the bedsore management device 220 sets medical dressing to hydrocolloid dressing (871).

When the answer to the question of how deep the wound is exceeds one point and is less than or equal to two points, the bedsore management device 220 sets medical dressing to hydrocolloid dressing (873).

When the answer to the question of how deep the wound is three points or more, the bedsore management device 220 sets medical dressing to hydrofiber dressing (875).

After setting medical dressing to hydrofiber dressing, the bedsore management device 220 checks an answer acquired from the bedsore management device 220 and/or the treatment integration device 240 to the question on the amount of exudate (877).

When the answer to the question on the amount of exudate is two points, the bedsore management device 220 checks an answer acquired from the bedsore management device 220 and/or the treatment integration device 240 to the question of how much epithelialization is present (879).

When the answer to the question of how much epithelialization is present is less than three points, the bedsore management device 220 sets medical dressing to hydrocolloid dressing (881).

When the answer to the question of how much epithelialization is present is three points or more, the bedsore management device 220 sets medical dressing to foam dressing (883).

When the answer to the question on the amount of exudate is three points, the bedsore management device 220 sets medical dressing to sterilized and adhesive dressing (885).

When the answer to the question on the amount of necrotic tissue is three points or more, the bedsore management device 220 checks an answer acquired from the bedsore management device 220 and/or the treatment integration device 240 to the question of how deep the wound is (887).

When the answer to the question of how deep the wound is less than two points, the bedsore management device 220 checks an answer acquired from the bedsore management device 220 and/or the treatment integration device 240 to the question on the amount of exudate (889).

When the answer to the question on the amount of exudate is two points, the bedsore management device 220 checks an answer acquired from the bedsore management device 220 and/or the treatment integration device 240 to the question of how much epithelialization is present (891).

When the answer to the question of how much epithelialization is present is less than three points, the bedsore management device 220 sets medical dressing to hydrocolloid dressing (893).

When the answer to the question of how much epithelialization is present is three points or more, the bedsore management device 220 sets medical dressing to foam dressing (895).

When the answer to the question on the amount of exudate is three points, the bedsore management device 220 sets medical dressing to sterilized and adhesive dressing (897).

When the answer to the question of how deep the wound is is two points or more, the bedsore management device 220 checks an answer acquired from the bedsore management device 220 and/or the treatment integration device 240 to the question on the amount of exudate (899).

When the answer to the question on the amount of exudate is two points, the bedsore management device 220 sets medical dressing to sterilized and adhesive dressing (901).

When the answer to the question on the amount of exudate is three points, the bedsore management device 220 sets medical dressing to hydrofiber dressing and sterilized and adhesive dressing (903).

When the answer to the question on the amount of exudate is four points, the bedsore management device 220 checks an answer acquired from the bedsore management device 220 and/or the treatment integration device 240 to the question of how deep the wound is (905).

When the answer to the question of how deep the wound is less than two points, the bedsore management device 220 checks an answer acquired from the bedsore management device 220 and/or the treatment integration device 240 to the question of how significant a change in the skin around the wound is (907). The current bedsore diagnosis information may include the answer information to the question of how significant a change in the skin around the wound is. The bedsore management device 220 may acquire the answer information to the question of how significant a change in the skin around the wound is on the basis of the machine learning model 710. In other words, the bedsore management device 220 may apply the bedsore image data of the current patient to the machine learning model 710 and acquire the answer information to the question of how significant a change in the skin around the wound is.

When the answer to the question of how significant a change in the skin around the wound is one point, the bedsore management device 220 sets medical dressing to sterilized and adhesive dressing (909).

When the answer to the question of how significant a change in the skin around the wound is two points or more, the bedsore management device 220 sets medical dressing to hydrofiber dressing (911).

After setting medical dressing to hydrofiber dressing, the bedsore management device 220 checks an answer acquired from the bedsore management device 220 and/or the treatment integration device 240 to the question of how much epithelialization is present (913).

When the answer to the question of how much epithelialization is present is less than three points, the bedsore management device 220 sets medical dressing to sterilized and adhesive dressing (915).

When the answer to the question of how much epithelialization is present is three points or more, the bedsore management device 220 sets medical dressing to foam dressing (917).

When the answer to the question of how deep the wound is two points or more, the bedsore management device 220 checks an answer acquired from the bedsore management device 220 and/or the treatment integration device 240 to the question on the amount of necrotic tissue (919).

When the answer to the question on the amount of necrotic tissue is less than three points, the process goes back to the operation 907, and the bedsore management device 220 checks an answer acquired from the bedsore management device 220 and/or the treatment integration device 240 to the question of how significant a change in the skin around the wound is (921). Subsequently, the bedsore management device 220 performs the process following the operation 907.

When the answer to the question on the amount of necrotic tissue is three points or more, the bedsore management device 220 checks an answer acquired from the bedsore management device 220 and/or the treatment integration device 240 to the question of how significant a change in the skin around the wound is (923).

When the answer to the question of how significant a change in the skin around the wound is one point, the bedsore management device 220 sets medical dressing to sterilized and adhesive dressing (925).

When the answer to the question of how significant a change in the skin around the wound is two points or more, the bedsore management device 220 sets medical dressing to hydrofiber dressing (927).

When the answer to the question of how significant a change in the skin around the wound is two points or more, the bedsore management device 220 sets medical dressing to sterilized and adhesive dressing in addition to hydrofiber dressing (929).

When the answer to the question on the amount of exudate is five points, the bedsore management device 220 sets medical dressing to hydrofiber dressing (929).

Figure 11:
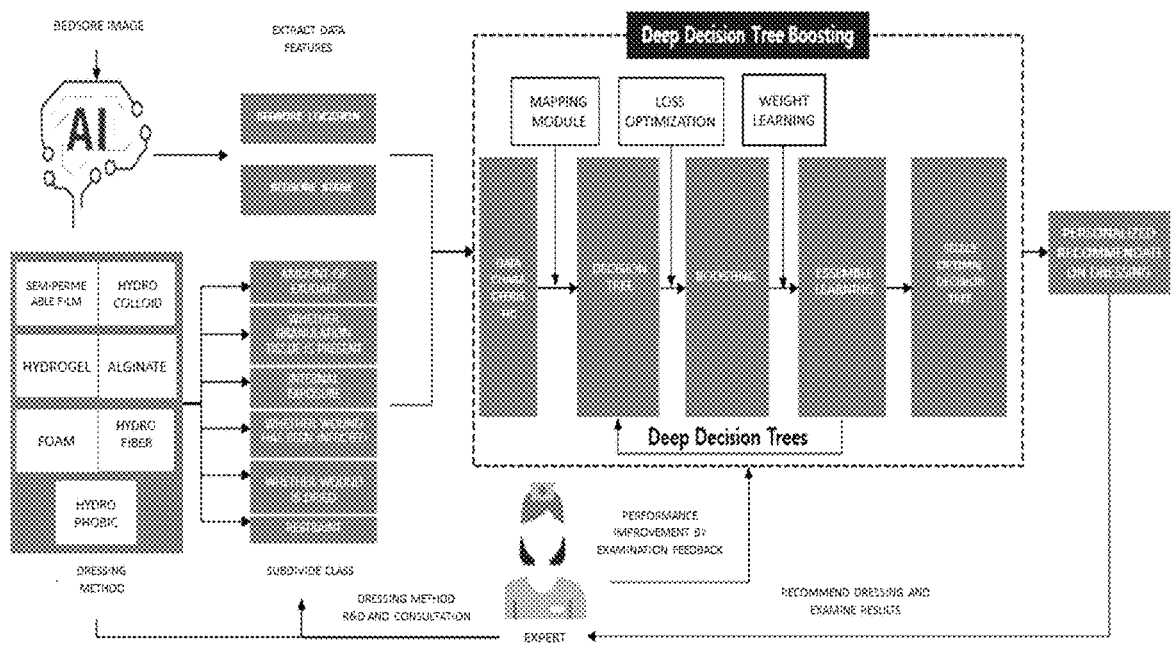
FIG. 11 is a diagram illustrating an example of operational flow of a bedsore management device according to an exemplary embodiment of the present disclosure.

FIG. 11 is a diagram illustrating an example of operational flow of a bedsore management device according to an exemplary embodiment of the present disclosure.

As described above, a bedsore management device according to the exemplary embodiment of the present disclosure may perform machine learning on relationships between image data of a plurality of existing bedsores and information on the plurality of existing bedsores and extract feature information of the image data of the plurality of existing bedsores. For example, the feature information of the image data of the plurality of existing bedsores may include location information which represents bedsore regions and bedsore stage information. Further, the information on the bedsores may include diagnosis information corresponding to the image data of the bedsores. The diagnosis information may include content for subdividing classes of dressing methods. For example, the diagnosis information may include at least one of the amount of exudate, whether granulation tissue is present, internal exposure, whether the wound has been infected, whether the wound is dried, and a restraint.

To select an optimal dressing recommendation algorithm, the bedsore management device may apply a deep decision tree boosting model to the feature information and the diagnosis information of the image data of the existing bedsores.

Ensemble is a machine learning technique for achieving better performance than a single decision tree by combining several decision trees. According to ensemble techniques, several weak classifiers may be combined into a strong classifier such that the accuracy of a machine learning model may be improved. Lately, ensemble techniques have shown innovative performance in machine learning fields, such as computer vision, speech recognition, natural language processing, and signal processing. Ensemble techniques include various techniques such as boosting and bagging. A deep decision tree boosting model is obtained by applying an ensemble learning method called boosting to a basic decision tree. The deep decision tree boosting model is an algorithm for determining an optimal deep decision tree through machine learning by which weights may be given while a loss value is optimized.

According to an exemplary embodiment of the present disclosure, as shown in FIG. 11, the diagnosis information in which classes are subdivided may be input to a deep decision tree boosting algorithm as input values in connection with the feature information of the bedsore image data. The input information is output to a decision tree via a mapping module, subjected to a boosting operation so that loss may be optimized, and then subjected to an ensemble learning operation so that learning may be performed using weights. As a result, an optimal decision tree may be determined.

As described above, the bedsore management device according to the exemplary embodiment of the present disclosure may determine an optimal dressing method by applying the deep decision tree boosting model. Further, at least one medical expert may be asked for examination or consultation on the suitability of the determined decision tree. Subsequently, information updated by adding information on the examination or consultation result may be input to the deep decision tree boosting algorithm. In this way, the accuracy of dressing recommendation may be continuously improved by reflecting feedback of experts.

Figure 12:
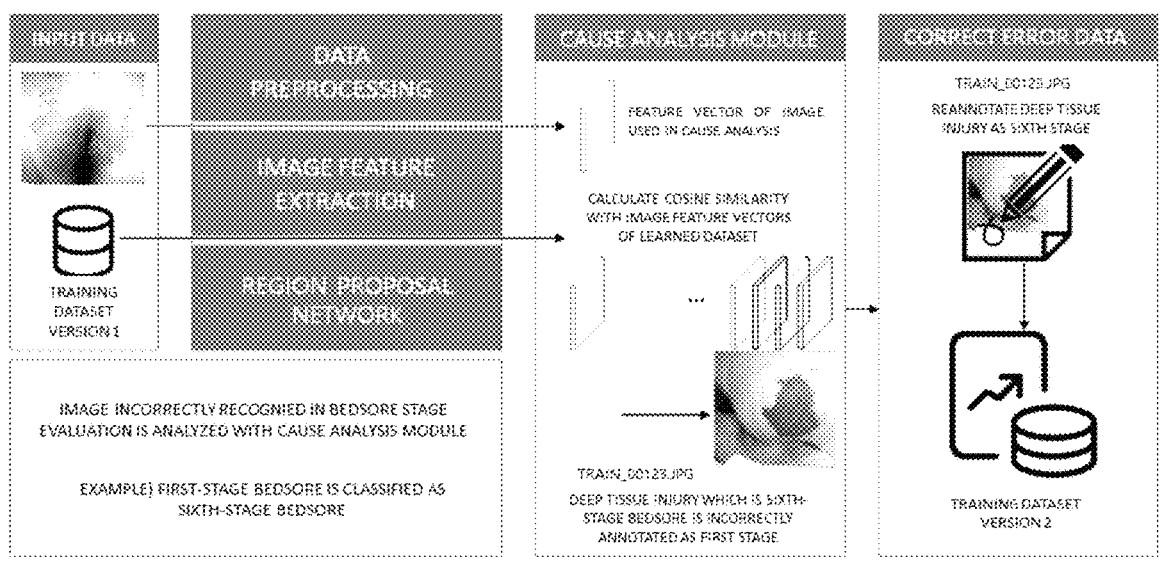
FIG. 12 is a diagram illustrating an example of an evaluation process of a machine learning model according to an exemplary embodiment of the present disclosure.

FIG. 12 is a diagram illustrating an example of an evaluation process of a machine learning model according to an exemplary embodiment of the present disclosure.

To increase learning and inference rates and accuracy of a machine learning model, the model evaluator 114 shown in FIG. 1 may perform cause analysis, evaluation, and handling on errors or efficiency degradation through the process illustrated in FIG. 12.

According to an exemplary embodiment of the present disclosure, to increase a machine learning rate, an inference rate, and accuracy, at least one factor among a model parameter, a hyperparameter, a GPU, and 16-bit calculation may be adjusted to be optimized.

The model parameter is a parameter obtained from internal data of the machine learning model and is automatically determined by modeling rather than a parameter input by a user. The hyperparameter is a parameter to be set in advance before the model is trained and differs from a parameter of the machine learning model that learns through training. The performance of the machine learning model may significantly vary depending on a value of the hyperparameter.

The model evaluator 114 may transmit a command to the model trainer 113 to perform distributed GPU training for optimizing multi-GPU learning.

To reduce memory and time required for machine learning, the model evaluator 114 may transmit a command to the model trainer 113 to perform mixed precision training.

To increase efficiency of an RPN operation, the model evaluator 114 may analyze annotated data and transmit size and ratio information of an optimized RPN anchor box to the model trainer 113.

According to an exemplary embodiment of the present disclosure, to increase reliability and accuracy of machine learning data, the model evaluator 114 may find and remove incorrect training data that degrades accuracy of training.

When an incorrect bedsore stage evaluation is made from bedsore image data, for example, when a bedsore in a first stage is incorrectly classified as a sixth stage, the model evaluator 114 may extract an image feature vector to be used in cause analysis from the image data, calculate cosine similarities between the extracted image feature vector and image feature vectors of learned datasets, detect N pieces of training data having the highest similarity in the datasets, and determine that annotation processing on bedsore stage information of the image data is incorrect. Subsequently, the model evaluator 114 may perform annotation processing for correcting the bedsore stage information or remove the data whose annotation is incorrect from the datasets. In this way, the datasets can be optimized, and accuracy and reliability of machine learning can be increased.

According to the inventive device for managing bedsores and the inventive operating method of the device, machine learning is performed with the relationships between bedsore photos and bedsore-related information to evaluate a bedsore stage and recommend medical dressing accordingly. Therefore, it is expected to reduce medical expenses and increase the efficiency of medical service. Also, it is possible to reduce the difference in nursing performance dependent on the experience of medical staff, and the effect of reducing the workload can be expected. Further, a change in the bedsore state of a patient can be continuously checked through system interoperation without using special equipment, and bedsore management can be intensively performed. Accordingly, it is possible to reduce the death rate of bedsore patients, shorten hospital stays, and reduce medical expenses.

According to the inventive device for managing bedsores and the inventive operating method of the device, machine learning is performed with the relationships between bedsore photos and bedsore-related information to evaluate a bedsore stage and recommend medical dressing accordingly. Therefore, it is expected to reduce medical expenses and increase the efficiency of medical service.

Various embodiments have been described above. Those of ordinary skill in the art should understand that the present disclosure can be embodied in modified forms without departing from essential characteristics of the present disclosure. Therefore, the disclosed embodiments should be considered in an illustrative sense rather than a restrictive sense. The scope of the present disclosure is shown in the claims rather than the above descriptions, and all differences within the equivalent scope should be interpreted as being included in the present disclosure.

Meanwhile, the above-described embodiments of the present disclosure can be written as a program that is executable on a computer and can be implemented on a general-purpose digital computer that executes the program using computer-readable recording media. The computer-readable recording media include storage media such as magnetic storage media (e.g., a ROM, a floppy disk, a hard disk, etc.) and optical media (e.g., a compact disc read-only memory (CD-ROM), a digital versatile disc (DVD), etc.).

What is claimed is:

1. An operating method of a bedsore management device, the operating method comprising:
    acquiring image data of a plurality of existing bedsores;
    acquiring existing bedsore-related information corresponding to the image data of the plurality of existing bedsores;
    training a convolutional neural network (CNN) with relationships between the image data of the plurality of existing bedsores and the existing bedsore-related information to acquire a machine learning model;
    acquiring bedsore image data of a current patient;
    applying the machine learning model to the bedsore image data of the current patient to determine information on a bedsore or bedsore treatment information of the current patient; and
    outputting the information on the bedsore or the bedsore treatment information of the current patient,
    wherein the existing bedsore-related information includes at least one of bedsore stage information of the existing bedsores, bedsore diagnosis information of the existing bedsores, bedsore location information of the existing bedsores in the image data, and existing bedsore treatment information of the existing bedsores,
    the information on the bedsore of the current patient includes at least one of bedsore stage information and bedsore diagnosis information of the current patient, and
    the bedsore treatment information includes dressing information for treating a bedsore.

2. The operating method of claim 1, wherein the training of the CNN with the relationships between the image data of the plurality of existing bedsores and the existing bedsore-related information to acquire the machine learning model comprises:
    preprocessing the image data of the plurality of existing bedsores;
    extracting image feature data from the preprocessed image data;
    training a region-based convolutional neural network (R-CNN) with relationships between the image data of the plurality of existing bedsores and the bedsore stage information of the existing bedsores using the image feature data; and
    outputting information on relationships between the bedsore location information and the bedsore stage information of the plurality of existing bedsores.

3. The operating method of claim 2, wherein the preprocessing of the image data of the plurality of existing bedsores comprises performing annotation processing on the image data of the plurality of existing bedsores, and
    the training of the R-CNN with the relationships between the image data of the plurality of existing bedsores and the bedsore stage information of the existing bedsores comprises using a region proposal network (RPN).

4. The operating method of claim 1, wherein the applying of the machine learning model to the bedsore image data of the current patient to determine the information on the bedsore or the bedsore treatment information of the current patient comprises determining dressing information required for treating the bedsore according to at least one of the bedsore stage information and the bedsore diagnosis information using a dressing recommendation algorithm,
wherein the dressing recommendation algorithm is determined using a deep decision tree boosting model.

5. The operating method of claim 2, wherein the applying of the machine learning model to the bedsore image data of the current patient to determine the information on the bedsore or the bedsore treatment information of the current patient comprises determining dressing information required for treating the bedsore according to at least one of the bedsore stage information and the bedsore diagnosis information using a dressing recommendation algorithm,
wherein the dressing recommendation algorithm is determined using a deep decision tree boosting model.

6. The operating method of claim 3, wherein the applying of the machine learning model to the bedsore image data of the current patient to determine the information on the bedsore or the bedsore treatment information of the current patient comprises determining dressing information required for treating the bedsore according to at least one of the bedsore stage information and the bedsore diagnosis information using a dressing recommendation algorithm,
wherein the dressing recommendation algorithm is determined using a deep decision tree boosting model.

7. A device for managing a bedsore, the device comprising a processor and a memory,
wherein, on the basis of instructions stored in the memory, the processor performs:
acquiring image data of a plurality of existing bedsores;
acquiring existing bedsore-related information corresponding to the image data of the plurality of existing bedsores;
training a convolutional neural network (CNN) with relationships between the image data of the plurality of existing bedsores and the existing bedsore-related information to acquire a machine learning model;
acquiring bedsore image data of a current patient;
applying the machine learning model to the bedsore image data of the current patient to determine information on a bedsore and bedsore treatment information of the current patient; and
outputting the information on the bedsore or the bedsore treatment information of the current patient,
wherein the existing bedsore-related information includes at least one of bedsore stage information, bedsore diagnosis information, and existing bedsore treatment information of the existing bedsores,
the information on the bedsore of the current patient includes at least one of bedsore stage information and bedsore diagnosis information of the current patient, and
the bedsore treatment information includes dressing information for treating the bedsore.

8. The device of claim 7, wherein, in order for the training of the relationships between the image data of the plurality of existing bedsores and the existing bedsore-related information and acquire the machine learning model, on the basis of the instructions stored in the memory, the processor performs:
preprocessing the image data of the plurality of existing bedsores;
extracting image feature data from the preprocessed image data;
training a region-based convolutional neural network (R-CNN) with relationships between the image data of the plurality of existing bedsores and the bedsore stage information of the existing bedsores using the image feature data; and
outputting information on relationships between bedsore location information and the bedsore stage information of the plurality of existing bedsores.

9. The device of claim 8, wherein, in order for the preprocessing of the image data of the plurality of existing bedsores, on the basis of the instructions stored in the memory, the processor performs annotation processing on the image data of the plurality of existing bedsores, and
in order for the training of the R-CNN with the relationships between the image data of the plurality of existing bedsores and the bedsore stage information of the existing bedsores, on the basis of the instructions stored in the memory, the processor may perform machine learning using an RPN.

10. The device of claim 7, wherein, in order for the applying of the machine learning model to the bedsore image data of the current patient and determine the information on the bedsore and the bedsore treatment information of the current patient, on the basis of the instructions stored in the memory, the processor determines dressing information required for treating the bedsore according to at least one of the bedsore stage information and the bedsore diagnosis information using a dressing recommendation algorithm,
wherein the dressing recommendation algorithm is determined using a deep decision tree boosting model.

11. The device of claim 8, wherein, in order for the applying of the machine learning model to the bedsore image data of the current patient and determine the information on the bedsore and the bedsore treatment information of the current patient, on the basis of the instructions stored in the memory, the processor determines dressing information required for treating the bedsore according to at least one of the bedsore stage information and the bedsore diagnosis information using a dressing recommendation algorithm,
wherein the dressing recommendation algorithm is determined using a deep decision tree boosting model.

12. The device of claim 9, wherein, in order for the applying of the machine learning model to the bedsore image data of the current patient and determine the information on the bedsore and the bedsore treatment information of the current patient, on the basis of the instructions stored in the memory, the processor determines dressing information required for treating the bedsore according to at least one of the bedsore stage information and the bedsore diagnosis information using a dressing recommendation algorithm,
wherein the dressing recommendation algorithm is determined using a deep decision tree boosting model.

* * * * *